(12) United States Patent
Kotani et al.

(10) Patent No.: US 11,109,828 B2
(45) Date of Patent: Sep. 7, 2021

(54) METAL X-RAY GRID, X-RAY IMAGING DEVICE, AND PRODUCTION METHOD FOR METAL X-RAY GRID

(71) Applicant: HAMAMATSU PHOTONICS K.K., Hamamatsu (JP)

(72) Inventors: Masahiro Kotani, Hamamatsu (JP); Hiroki Kawakami, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 78 days.

(21) Appl. No.: 16/500,192

(22) PCT Filed: Feb. 27, 2018

(86) PCT No.: PCT/JP2018/007303
§ 371 (c)(1),
(2) Date: Oct. 2, 2019

(87) PCT Pub. No.: WO2018/186059
PCT Pub. Date: Oct. 11, 2018

(65) Prior Publication Data
US 2021/0093273 A1    Apr. 1, 2021

(30) Foreign Application Priority Data
Apr. 5, 2017 (JP) .............................. JP2017-075431

(51) Int. Cl.
*A61B 6/00* (2006.01)
*G21K 1/06* (2006.01)

(52) U.S. Cl.
CPC .............. *A61B 6/484* (2013.01); *G21K 1/067* (2013.01); *G21K 2201/064* (2013.01); *G21K 2201/067* (2013.01)

(58) Field of Classification Search
None
See application file for complete search history.

(56) References Cited

U.S. PATENT DOCUMENTS

2013/0343524 A1*  12/2013  Teshima ........... G01N 23/20008
                                                            378/71
2015/0092918 A1    4/2015  Crocco et al.
(Continued)

FOREIGN PATENT DOCUMENTS

| EP | 3127861 A1 | 2/2017 |
|----|------------|--------|
| JP | H11-104119 A | 4/1999 |

(Continued)

OTHER PUBLICATIONS

International Preliminary Report on Patentability (IPRP) dated Oct. 17, 2019 that issued in WO Patent Application No. PCT/JP2018/007303.

(Continued)

*Primary Examiner* — Hoon K Song
(74) *Attorney, Agent, or Firm* — Faegre Drinker Biddle & Reath LLP

(57) ABSTRACT

A metal grid includes: a valve metal plate which includes a curved principal surface; an anodic oxide film which is formed on the principal surface of the valve metal plate; and a lattice structure which has an uneven shape periodically formed on the anodic oxide film. Further, a production method for a metal grid includes: a step of bending a principal surface of a valve metal plate including the principal surface; a step of forming an anodic oxide film on the principal surface of the valve metal plate; and a step of forming a lattice structure with a periodic uneven shape on the anodic oxide film by forming an etching mask with a periodic opening on a surface of the anodic oxide film and etching the anodic oxide film through the opening.

11 Claims, 22 Drawing Sheets

(56) References Cited

U.S. PATENT DOCUMENTS

| | | | |
|---|---|---|---|
| 2015/0316494 A1 | 11/2015 | Teshima et al. | |
| 2016/0265125 A1* | 9/2016 | Yokoyama | C25D 7/00 |
| 2016/0293284 A1* | 10/2016 | Yokoyama | C25D 7/12 |

FOREIGN PATENT DOCUMENTS

| | | |
|---|---|---|
| JP | 2011-69818 A | 4/2011 |
| JP | 2012-13530 A | 1/2012 |
| JP | 2012-093332 A | 5/2012 |
| JP | 2014-6194 A | 1/2014 |
| JP | 5627247 B2 | 11/2014 |
| JP | 2015-127702 A | 7/2015 |
| JP | 2015-221192 A | 12/2015 |
| JP | 2016-211912 A | 12/2016 |
| JP | 2017-32476 A | 2/2017 |
| JP | 6217381 B2 | 10/2017 |
| WO | WO-2017/036729 A1 | 3/2017 |

OTHER PUBLICATIONS

Masuda et al., "Ordered Metal Nanohole Arrays Made by a Two-Step Replication of Honeycomb Structures of Anodic Alumina", Science, American Association for the Advancement of Science, US, vol. 268, Jun. 9, 1995, p. 1466-p. 1468, XP000770000.

* cited by examiner (a)

(b)

(c)

(a)

(b)

(c)

(a)

(b)

METAL X-RAY GRID, X-RAY IMAGING DEVICE, AND PRODUCTION METHOD FOR METAL X-RAY GRID

TECHNICAL FIELD

An aspect of the invention relates to a metal X-ray grid, an X-ray imaging device, and a production method for the metal X-ray grid.

BACKGROUND ART

Patent Literature 1 describes a technique relating to a metal X-ray grid and a production method thereof. In the production method described in this literature, a first region with a resist layer and a second region without a resist layer are first formed on one principal surface of a metal substrate. Next, a plurality of holes are formed in the metal substrate corresponding to the second region by an anodic oxidation method. Next, the resist layer of the first region is removed so that a concave portion is formed in the metal substrate corresponding to the first region. Next, an X-ray absorbing material is filled in the concave portion.

CITATION LIST

Patent Literature

Patent Literature 1: Japanese Unexamined Patent Publication No. 2016-211912

SUMMARY OF INVENTION

Technical Problem

For example, in an X-ray related field such as an X-ray imaging device, a metal grid in which a region (an X-ray passing region) of relatively high X-ray transmittance and a region (an X-ray shielding region) of relatively low X-ray transmittance are periodically arranged is used in some cases. As an example, a plurality of metal grids are used in an X-ray imaging device that uses an interferometer such as a Talbot interferometer or a Talbot-Lau interferometer. It is preferable that the metal grid has a microscopic structure of a high aspect ratio in which an X-ray passing region and an X-ray shielding region are respectively, for example, several μm in width and several tens of μm in thickness. In a conventional metal grid production method, a surface of a substrate of a certain material is etched to form a lattice structure and a void formed by the etching is filled with metal (for example, gold (Au)) of low X-ray transmittance if necessary. In the metal grid which is produced in this way, the extension direction in the substrate of the X-ray passing region is perpendicular to a surface of the substrate. For example, in the metal X-ray grid described in Patent Literature 1, the surface of the substrate is flat and the extension directions of all X-ray passing regions are parallel to one another.

When the extension directions of all X-ray passing regions are parallel to one another, the following problem arises. That is, when X-rays radially spreading from a dot-shaped X-ray source are received by the metal grid, a relative angle between the traveling direction of the incident X-ray and the extension direction of the X-ray passing region increases as the distance from the center of the metal grid increases and hence the desired function of the metal grid is not easily obtained. Thus, an area where the X-rays are incident is limited.

Furthermore, Patent Literature 1 describes a configuration illustrated in FIG. 22. In this configuration, a plurality of holes 102 are formed as an X-ray passing region so as to converge toward a focal point of X-rays XL emitted from an X-ray source 101. However, it is extremely difficult to form a plurality of microscopic holes 102 each having a high aspect ratio and an inclined extension direction in a planar member.

An aspect of the invention has been made in view of such a problem and an object thereof is to provide a metal X-ray grid, an X-ray imaging device, and a production method for a metal X-ray grid capable of obtaining a desired function even at a position far from a center and further widening an area where X-rays are incident.

Solution to Problem

A metal X-ray grid according to an embodiment of the invention includes: a valve metal plate which includes a curved principal surface; an anodic oxide film which is formed on the principal surface of the valve metal plate; and a lattice structure which has an uneven shape periodically formed on the anodic oxide film. In this metal X-ray grid, when the concave portion of the uneven shape is a void or the concave portion is filled with a material of X-ray transmittance higher than that of the anodic oxide film, the inside of the concave portion becomes an X-ray passing region and the anodic oxide film remaining in the convex portion becomes an X-ray shielding region. Further, when the concave portion is filled with a material of X-ray transmittance lower than that of the anodic oxide film, the inside of the concave portion becomes an X-ray shielding region and the anodic oxide film remaining in the convex portion becomes an X-ray passing region.

Further, in the metal X-ray grid, the principal surface of the valve metal plate is curved. Accordingly, the extension direction of the X-ray passing region is also slightly inclined in accordance with the curvature of the principal surface. Thus, it is possible to decrease a relative angle between the traveling direction of the X-rays incident to the X-ray passing region and the extension direction of the X-ray passing region when receiving the X-rays radially spreading from a dot-shaped X-ray source regardless of the distance from the center of the metal X-ray grid by setting the curvature of the principal surface in accordance with the distance from the X-ray source. Thus, according to the metal X-ray grid, it is possible to obtain a desired function even at a position far from a center and to further widen an area where X-rays are incident.

In the metal X-ray grid, a side surface of the uneven shape may be perpendicular to the principal surface. Accordingly, X-rays can efficiently pass in the X-ray passing region.

The metal X-ray grid may further include: at least one of a frame portion which supports a peripheral edge portion of the valve metal plate and a support substrate which is affixed to the valve metal plate and supports the valve metal plate. Accordingly, since it is possible to maintain the mechanical strength of the metal X-ray grid even when the valve metal plate is thin, it is possible to reduce the loss of X-rays when the X-rays are transmitted through the valve metal plate by thinning the valve metal plate.

The metal X-ray grid may further include: a metal portion which contains metal of X-ray transmittance lower than that of valve metal of the valve metal plate and fills a concave portion of the lattice structure. As described above, in this case, the metal portion (the concave portion) becomes an X-ray shielding region and the anodic oxide film between the metal portions becomes an X-ray passing region. Then, also in such a case, the effects of the above-described metal X-ray grid can be appropriately achieved.

The metal X-ray grid may further include: a protective film which is provided on a region excluding the concave portion of the anodic oxide film. By using such a protective film, it is possible to effectively prevent a variation in X-ray transmittance due to a foreign matter infiltrating into the hole of the porous anodic oxide film. Further, it is possible to effectively prevent metal from infiltrating into the hole of the porous anodic oxide film by the protective film when forming the metal portion. This protective film may be an etching mask used to form the concave portion by etching the anodic oxide film. In general, the X-ray transmittance of the etching mask used when etching the anodic oxide film is extremely high. Thus, the loss of X-rays is slight even when the etching mask remains in the completed metal X-ray grid. On the other hand, it is possible to reduce production cost by omitting the step of removing the etching mask in the production step of the metal X-ray grid.

In the metal X-ray grid, the protective film may contain resin. In this way, since the protective film contains resin which is a material having extremely high X-ray transmittance, it is possible to extremely reduce the loss of X-rays when the X-rays are transmitted through the protective film.

Further, an X-ray imaging device according to an embodiment of the invention includes: an X-ray source which emits X-rays; a Talbot interferometer or a Talbot-Lau interferometer which is irradiated with the X-rays emitted from the X-ray source; and an X-ray imaging unit which captures an X-ray image emitted from the Talbot interferometer or the Talbot-Lau interferometer, in which the Talbot interferometer or the Talbot-Lau interferometer includes any one of the above-described metal X-ray grids. According to this X-ray imaging device, since the Talbot interferometer or the Talbot-Lau interferometer includes any one of the above-described metal X-ray grids, a larger area can be captured.

Further, a production method for a metal X-ray grid according to an embodiment of the invention includes: a step of bending a principal surface of a valve metal plate including the principal surface; a step of forming an anodic oxide film on the principal surface of the valve metal plate; and a step of forming a lattice structure with a periodic uneven shape on the anodic oxide film by forming an etching mask with a periodic opening on a surface of the anodic oxide film and etching the anodic oxide film through the opening.

In this production method, when the concave portion of the uneven shape is a void or the concave portion is filled with a material of X-ray transmittance higher than that of the anodic oxide film, the inside of the concave portion becomes an X-ray passing region and the anodic oxide film remaining in the convex portion becomes an X-ray shielding region. Further, when the concave portion is filled with a material of X-ray transmittance lower than that of the anodic oxide film, the inside of the concave portion becomes an X-ray shielding region and the anodic oxide film remaining in the convex portion becomes an X-ray passing region.

Further, in the production method, the principal surface of the valve metal plate is curved. Accordingly, the extension direction of the X-ray passing region which will be formed later is also slightly inclined in accordance with the curvature of the principal surface. Thus, it is possible to decrease a relative angle between the traveling direction of the X-rays incident to the X-ray passing region and the extension direction of the X-ray passing region when receiving the X-rays radially spreading from a dot-shaped X-ray source regardless of the distance from the center of the metal X-ray grid by setting the curvature of the principal surface in accordance with the distance from the X-ray source. Thus, according to the above-described production method, it is possible to provide the metal X-ray grid capable of obtaining a desired function even at a position far from a center and further widening an area where X-rays are incident.

The production method for the metal X-ray grid may further include: a step of forming a metal portion which contains metal of X-ray transmittance lower than that of valve metal of the valve metal plate and fills a concave portion of the lattice structure after the step of forming the lattice structure. As described above, in this case, the metal portion (the concave portion) becomes the X-ray shielding region and the anodic oxide film between the metal portions becomes the X-ray passing region. Then, also in such a case, the effects of the above-described production method can be appropriately achieved.

In the production method for the metal X-ray grid, in the step of forming the metal portion, the metal portion may be formed while the etching mask is left. In this case, it is possible to reduce production cost by omitting the step of removing the etching mask in the production step of the metal X-ray grid. Further, it is possible to effectively prevent metal from infiltrating into the hole of the porous anodic oxide film by the etching mask when forming the metal portion.

In the production method for the metal X-ray grid, in the step of forming the metal portion, the metal portion may be formed by any one of electrolytic plating, CVD, and ALD. Accordingly, it is possible to appropriately form the metal portion in the concave portion having a fine and high aspect ratio.

The production method for the metal X-ray grid may further include: a step of attaching at least one of a frame portion which supports a peripheral edge portion of the valve metal plate and a support substrate which is affixed to the valve metal plate and supports the valve metal plate. Accordingly, since it is possible to maintain the mechanical strength of the metal X-ray grid even when the valve metal plate is thin, it is possible to reduce the loss of X-rays when the X-rays are transmitted through the valve metal plate by thinning the valve metal plate.

Advantageous Effects of Invention

According to the metal X-ray grid, the X-ray imaging device, and the production method for the metal X-ray grid of an aspect of the invention, it is possible to obtain a desired function even at a position far from a center and to further widen an area where X-rays are incident.

DESCRIPTION OF EMBODIMENTS

Figure 1:
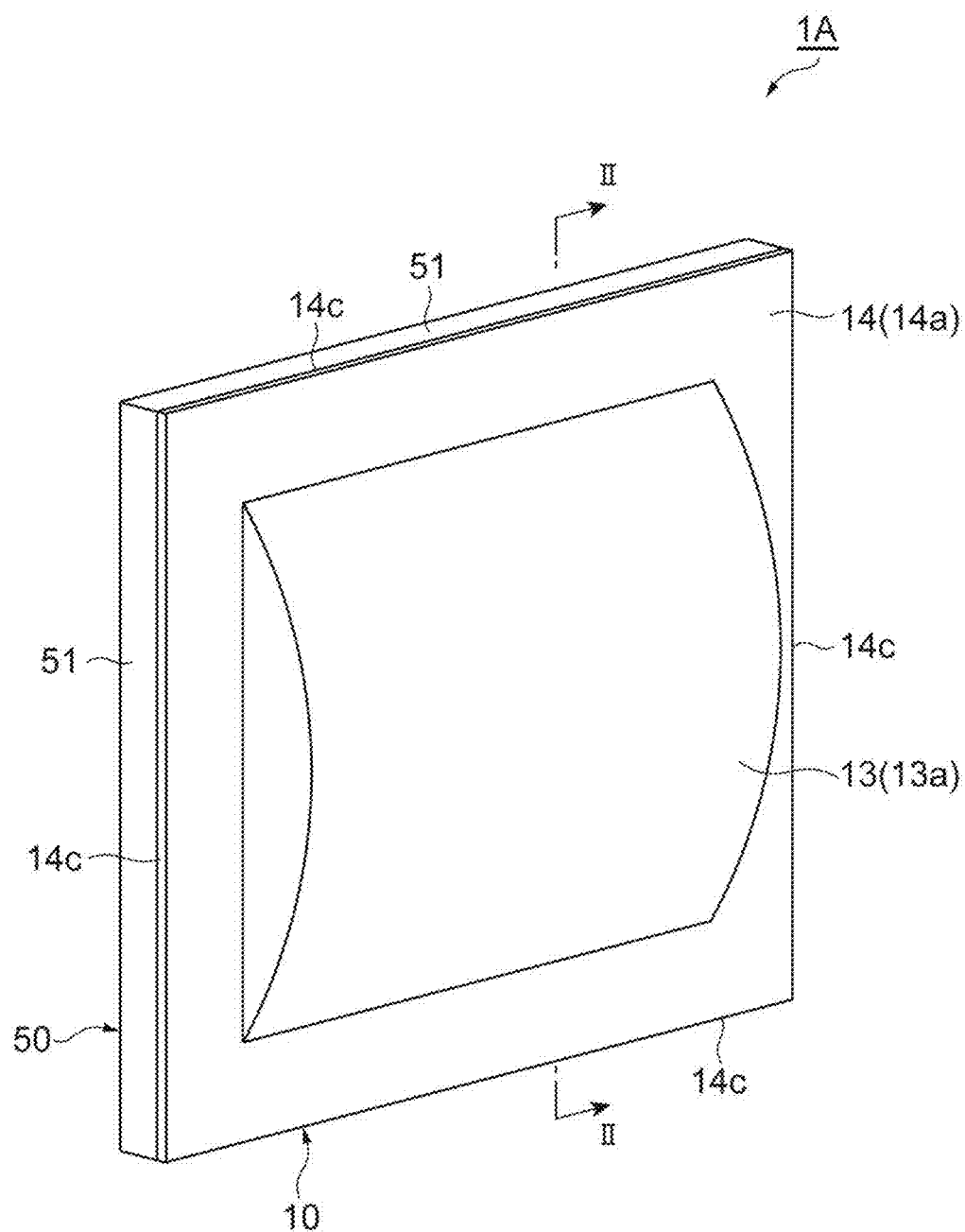
FIG. 1 is a perspective view illustrating a metal X-ray grid according to an embodiment of the invention.

Hereinafter, a metal X-ray grid, an X-ray imaging device, and a production method for the metal X-ray grid of an embodiment will be described in detail with reference to the accompanying drawings. Furthermore, in the description of the drawings, the same components will be denoted by the same reference numerals and a repetitive description thereof will be omitted.

First Embodiment

Figure 2:
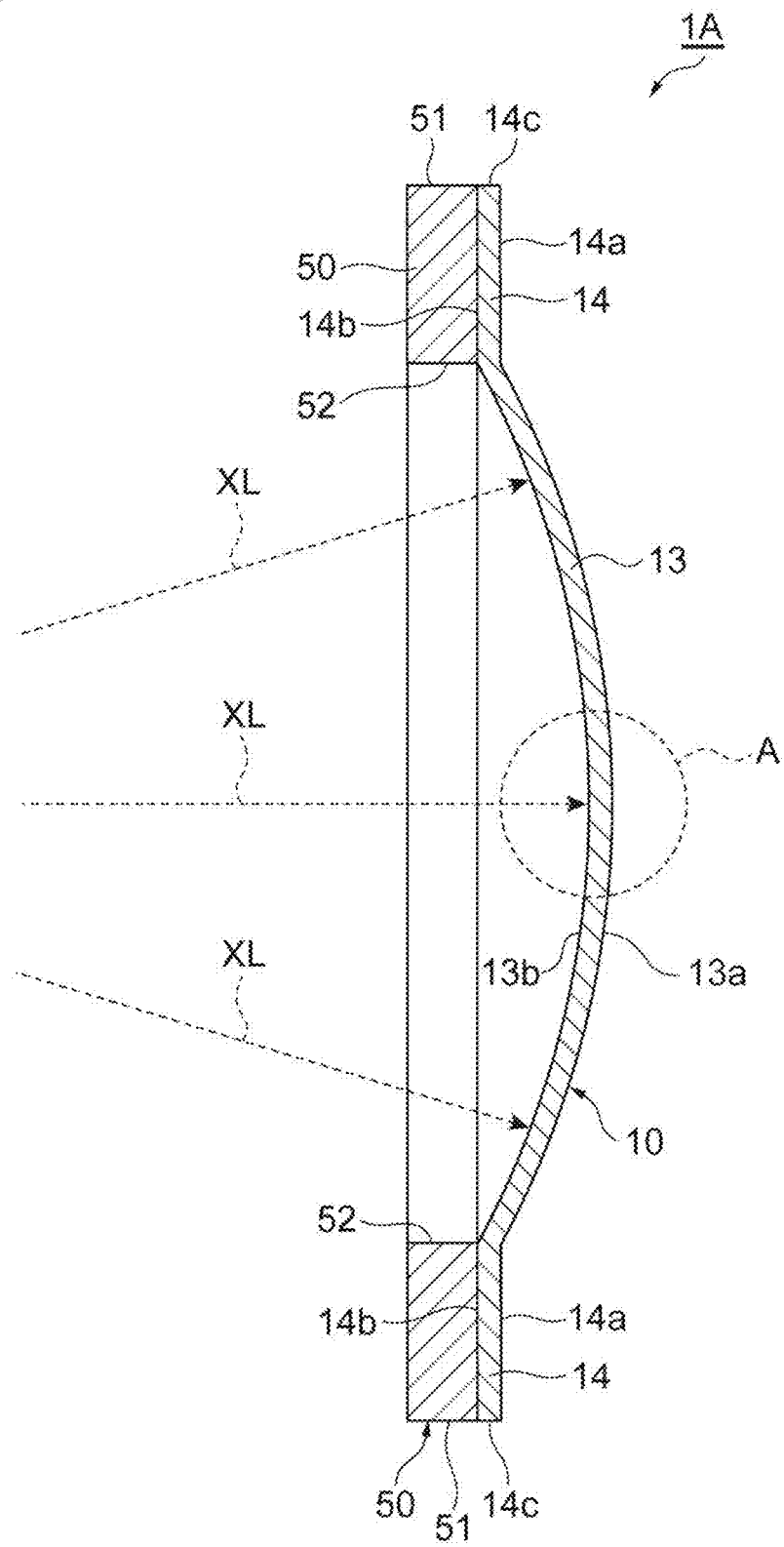
FIG. 2 is a cross-sectional view taken along a line II-II of FIG. 1.
Figure 3:
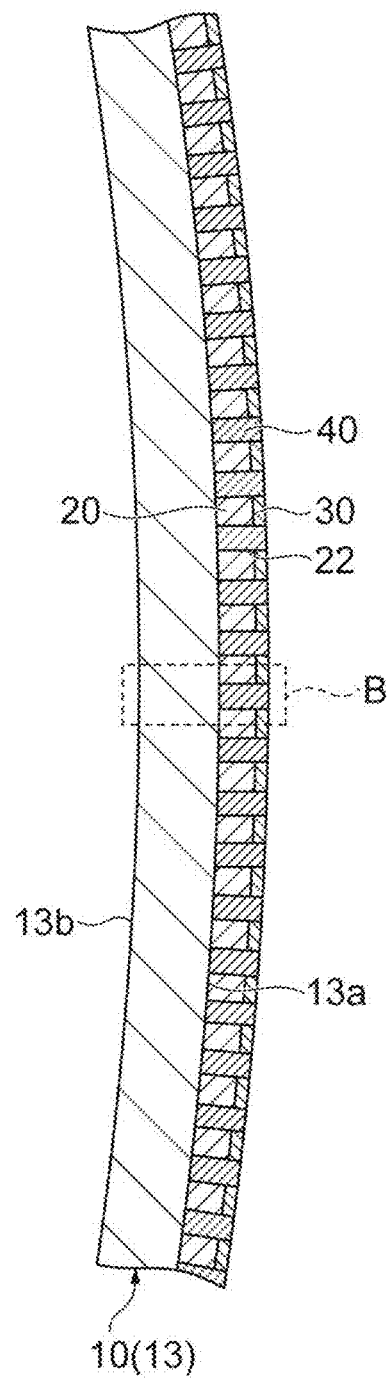
FIG. 3 is an enlarged cross-sectional view of an A part of FIG. 2.

FIG. 1 is a perspective view illustrating a metal X-ray grid (hereinafter, referred to as a metal grid) 1A according to an embodiment of the invention. FIG. 2 is a cross-sectional view taken along a line II-II of FIG. 1 and FIG. 3 is an enlarged cross-sectional view of an A part of FIG. 2. FIG. 2 illustrates X-rays XL which are incident to the metal grid 1A. The metal grid 1A of the embodiment is used as an X-ray diffraction grating, for example, in an X-ray device such as an X-ray imaging device using a Talbot interferometer or a Talbot-Lau interferometer. As illustrated in FIGS. 1 to 3, the metal grid 1A includes a metal plate 10 (a valve metal plate), an anodic oxide film 20, a protective film 30, a metal portion 40, and a frame portion 50.

The metal plate 10 is a plate which is formed of valve metal. The metal plate 10 includes an X-ray receiving portion 13 which includes a curved principal surface 13a and a curved rear surface 13b, and a flange portion 14 (a peripheral edge portion) which is provided in the periphery of the X-ray receiving portion 13 and includes a flat principal surface 14a and a rear surface 14b. The valve metal is metal capable of forming the anodic oxide film 20 and is, for example, at least one selected from a group of Al, Ta, Nb, Ti, Hf, Zr, Zn, W, Bi, and Sb. The thickness of the X-ray receiving portion 13 is, for example, 0.1 mm or more and 5.0 mm or less. The planar shapes of the X-ray receiving portion 13 and the flange portion 14 (the shape when viewed from the optical axis direction of the X-ray XL) are, for example, rectangular or square. The length of one side of the X-ray receiving portion 13 is, for example, 10 mm or more and 500 mm or less and the length of one side of the flange portion 14 is, for example, 11 mm or more and 600 mm or less.

Figure 4:
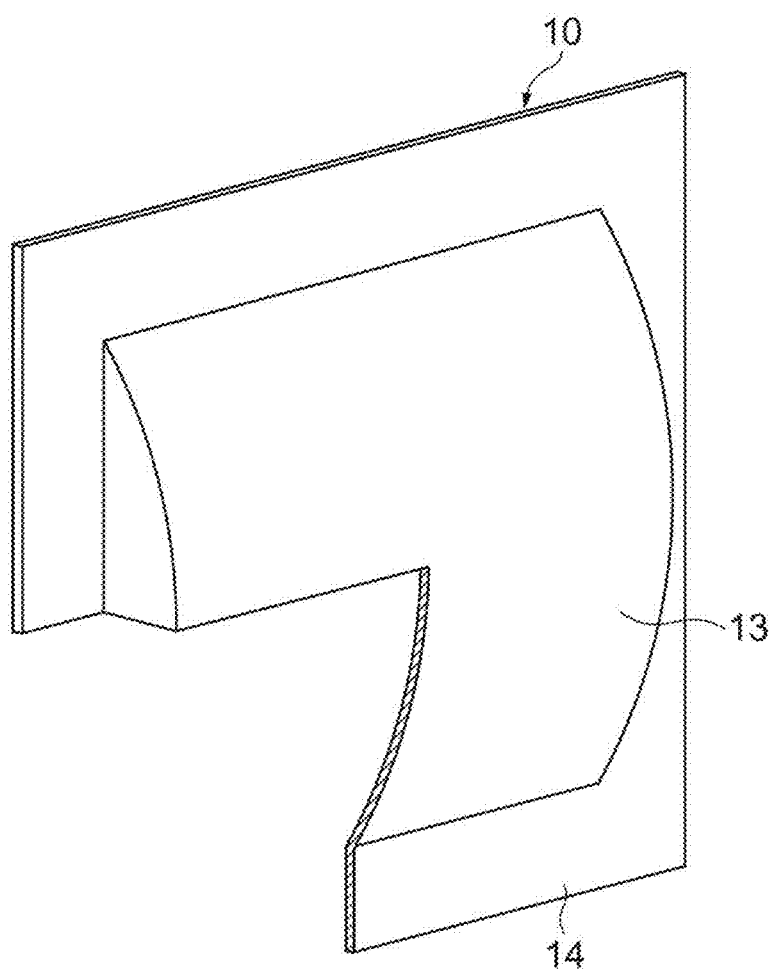
FIG. 4 is a perspective view illustrating a partially notched metal plate.

The curved principal surface 13a and the curved rear surface 13b of the X-ray receiving portion 13 are formed by bending, for example, the planar metal plate 10. FIG. 4 is a perspective view illustrating the partially notched metal plate 10. The X-ray receiving portion 13 of the embodiment has a shape with a one-dimensional curvature (a shape obtained by cutting a part of a cylindrical surface). In other words, the X-ray receiving portion 13 is curved in one cross-section including the optical axis of the X-ray XL, and is flat in a cross-section including the optical axis of the X-ray XL and perpendicular to the one cross-section. The curvature radius of the X-ray receiving portion 13 is, for example, 50 mm or more and 1000 mm or less and is 500 mm in one embodiment. This curvature radius is mainly determined in accordance with the distance from the X-ray source.

Figure 5:
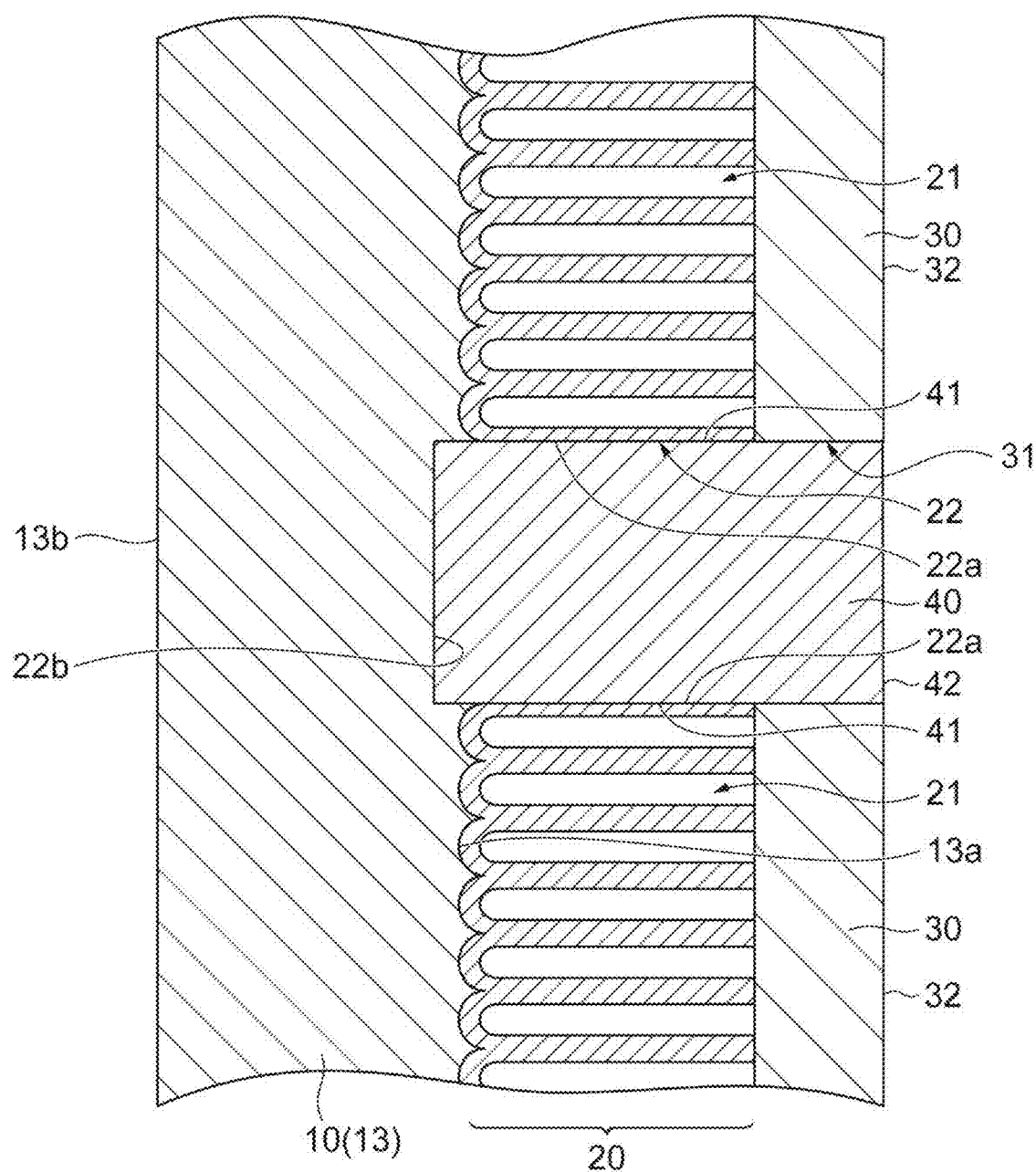
FIG. 5 is a cross-sectional view of a partially enlarged anodic oxide film.

The anodic oxide film 20 illustrated in FIG. 3 is formed on the principal surface 13a of the metal plate 10. The anodic oxide film 20 is formed by performing an anodic oxidation treatment on the principal surface 13a of the metal plate 10. FIG. 5 is a cross-sectional view of the partially enlarged anodic oxide film 20. As illustrated in FIG. 5, the anodic oxide film 20 is porous and includes a plurality of microscopic holes 21. These holes 21 extend in a direction perpendicular to the principal surface 13a and are regularly arranged along a plane parallel to the principal surface 13a. The planar shape of the hole 21 when viewed from a direction perpendicular to the principal surface 13a is circular. The inner diameter of the hole 21 is, for example, 40 nm. Furthermore, the planar shape of the hole 21 is not limited to a circular shape and may be other shapes such as a square shape.

Figure 6:
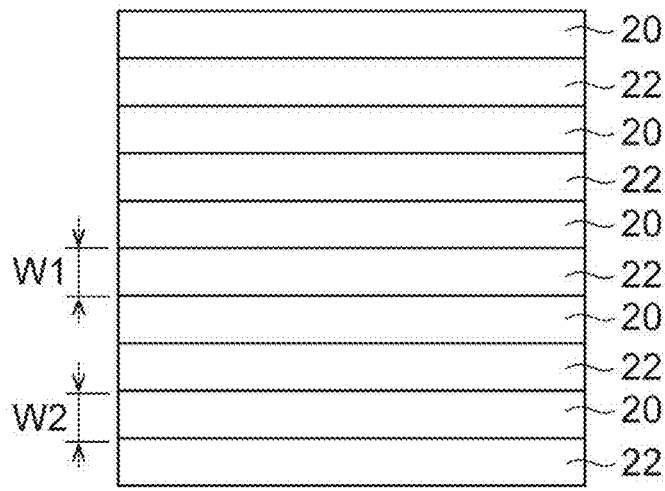
FIG. 6 is a view illustrating an example of a planar shape of a concave portion.
Figure 6:
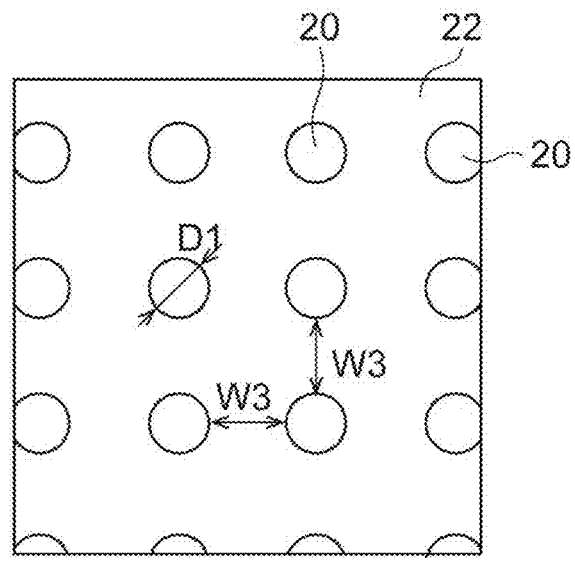
Figure 6:
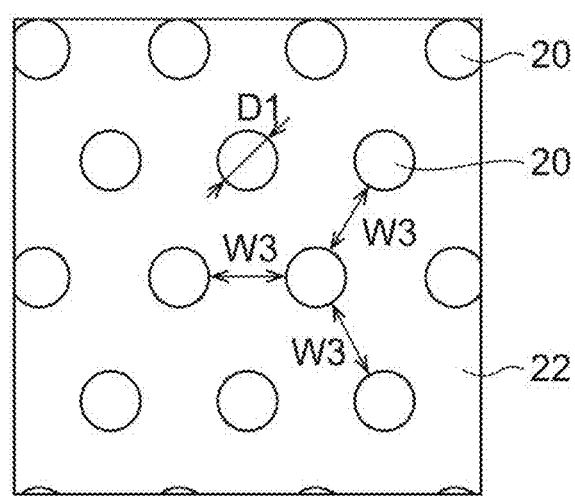

As illustrated in FIGS. 3 and 5, the anodic oxide film 20 is provided with a lattice structure having an uneven shape which is periodically formed. A concave portion 22 which constitutes the uneven shape extends in a direction perpendicular to the principal surface 13a and a side surface 22a of the concave portion 22 is perpendicular to the principal surface 13a. Further, in a cross-section illustrated in FIGS. 3 and 5, the concave portions 22 are arranged along a surface parallel to the principal surface 13a. A bottom surface 22b of the concave portion 22 reaches the metal plate 10. That is, the bottom surface 22b is formed of valve metal of the metal plate 10. FIGS. 6(a) to 6(c) are views illustrating an example of the planar shape of the concave portion 22. In the example illustrated in FIG. 6(a), the plurality of concave portions 22 extend in a predetermined direction along the principal surface 13a and are arranged at a predetermined interval in a direction orthogonal to the predetermined direction. In this case, the width W1 of the plurality of concave portions 22 in the arrangement direction is, for example, 0.1 μm or more and 20 μm or less and the gap W2 between the concave portions 22 adjacent to each other in that direction is, for example, 0.1 μm or more and 20 μm or less. Further, in the example illustrated in FIG. 6(b), the concave portions 22 surround a plurality of convex portions (the anodic oxide film 20) having a circular shape and the plurality of convex portions are arranged in a square lattice shape. In the example illustrated in FIG. 6(c), the concave portions 22 surround a plurality of convex portions (the anodic oxide film 20) having a circular shape and the plurality of convex portions are arranged in a triangular lattice shape. When the plurality of convex portions which are formed from the anodic oxide film 20 are circular, the inner diameter D1 of the plurality of convex portions is, for example, 0.1 μm or more and 20 μm or less and the gap W3 between the adjacent convex portions is, for example, 0.1 μm or more and 20 μm or less.

Again, FIGS. 3 and 5 are referred. The protective film 30 is provided on a region excluding the concave portion 22 of the anodic oxide film 20 (that is, on the plurality of convex portions formed from the anodic oxide film 20) and is in contact with the anodic oxide film 20. The protective film 30 includes an opening 31 corresponding to the concave portion 22 (see FIG. 5). As an example, the protective film 30 is an etching mask used to etch the anodic oxide film 20 for forming the concave portion 22 and remains on the metal grid 1A while not being removed even after the etching. The etching mask may be a so-called resist. The thickness of the protective film 30 is, for example, 0.1 μm or more and 1 mm or less.

The metal portion 40 is a portion which fills the concave portion 22. Since the metal portion 40 is disposed inside the concave portion 22, the planar shape and the arrangement thereof are the same as those of the concave portion 22. That is, the metal portion 40 have the same planar shape as that of the concave portion 22, for example, illustrated in FIGS. 6(a) to 6(c) and the metal portions are periodically arranged. When the concave portion 22 has a form illustrated in FIG. 6(a), the metal portions 40 extending in a predetermined direction along the principal surface 13a and having a thin plate shape are arranged at a predetermined interval in a direction orthogonal to the predetermined direction. Further, when the concave portion 22 has a form illustrated in FIG. 6(b) or FIG. 6(c), the metal portions 40 surround the plurality of anodic oxide films 20 having a columnar shape and the plurality of anodic oxide films 20 are arranged in a square lattice shape or a triangular lattice shape.

The metal portion 40 mainly contains metal of X-ray transmittance lower than that of the valve metal forming the metal plate 10. As an example, the metal portion 40 is formed of metal of X-ray transmittance lower than that of the valve metal forming the metal plate 10. As such metal, for example, at least one of a group of Au, W, Pt, and Pb can be exemplified. In the embodiment, the metal portion 40 functions as an X-ray shielding region. Since the side surface 22a of the concave portion 22 is perpendicular to the principal surface 13a of the metal plate 10, the side surface 41 of the metal portion 40 is also perpendicular to the principal surface 13a of the metal plate 10. Further, the metal portion 40 is in contact with the bottom surface 22b of the concave portion 22. Furthermore, in the embodiment, the top surface 42 of the metal portion 40 is substantially flush with the top surface 32 of the protective film 30, but the top surface 42 of the metal portion 40 may be lower than the top surface 32 of the protective film 30 or the metal portion 40 may cover the top surface 32 of the protective film 30.

Again, FIGS. 1 and 2 are referred. The frame portion 50 is a support member that is attached to the flange portion 14 of the metal plate 10. The frame portion 50 is provided to supplement the mechanical strength of the metal grid 1A and to improve the portability and easy installation of the metal grid 1A. The frame portion 50 of the embodiment has a planar shape which is a frame shape when viewed from a direction perpendicular to the principal surface 13a of the metal plate 10. The shape of the outer edge 51 of the frame portion 50 substantially matches the shape of the outer edge 14c of the flange portion 14 and the shape of the inner edge 52 of the frame portion 50 substantially matches the shape of the outer edge of the X-ray receiving portion 13. In other words, the planar shape of the frame portion 50 of the embodiment is a rectangular or square frame shape. Since the frame portion 50 of the embodiment does not overlap the X-ray receiving portion 13, the material and the thickness of the frame portion 50 are determined without considering X-ray transmittance (alternately, so that the unnecessary X-rays deviating from the X-ray receiving portion 13 are absorbed). The thickness of the frame portion 50 is, for example, 0.5 mm or more and 10 cm or less. The material of the frame portion 50 is, for example, SUS. The frame portion 50 and the flange portion 14 are bonded to each other by, for example, a resin adhesive. Furthermore, in FIG. 2, the frame portion 50 is provided on the side of the rear surface 14b of the flange portion 14, but the frame portion 50 may be provided on the side of the principal surface 14a of the flange portion 14 or the frame portion 50 may be provided on both sides of the principal surface 14a and the rear surface 14b.

Figure 7:
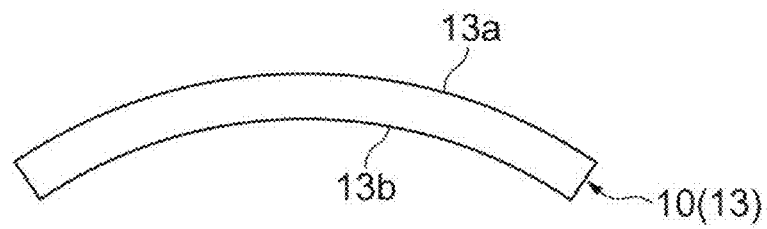
FIG. 7 is a view illustrating a metal grid production step.
Figure 7:
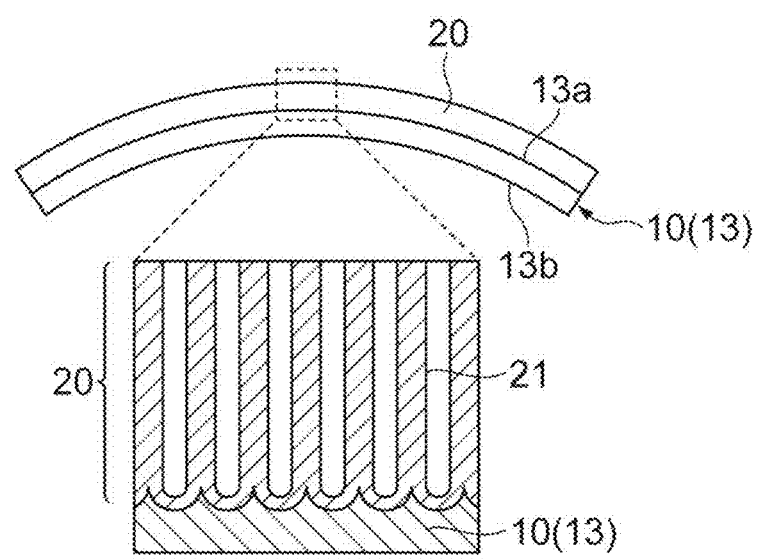
Figure 7:
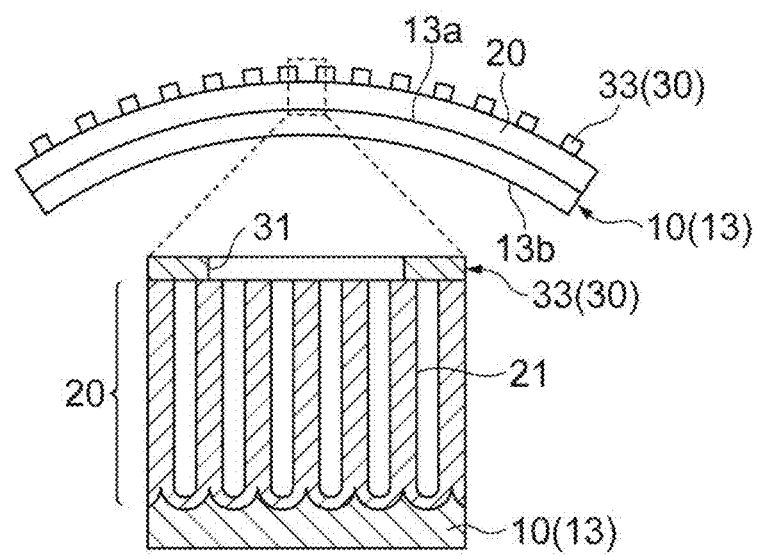
Figure 8:
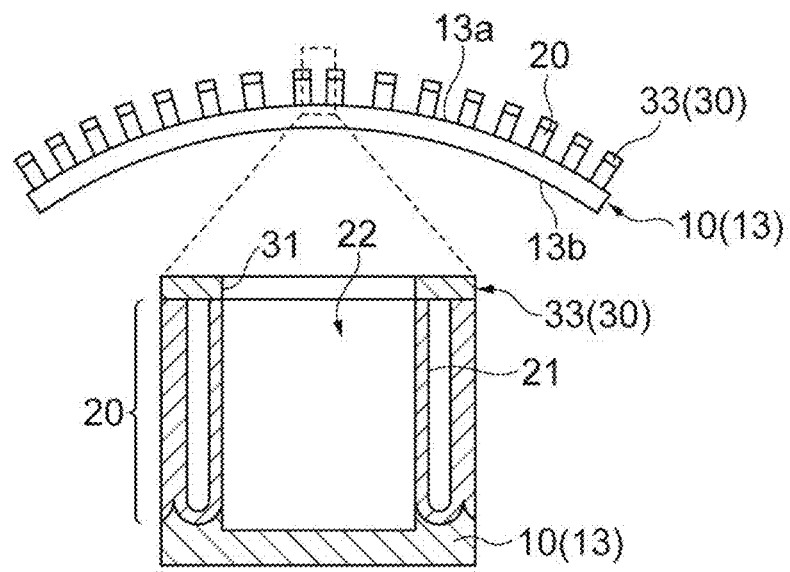
FIG. 8 is a view illustrating the metal grid production step.
Figure 8:
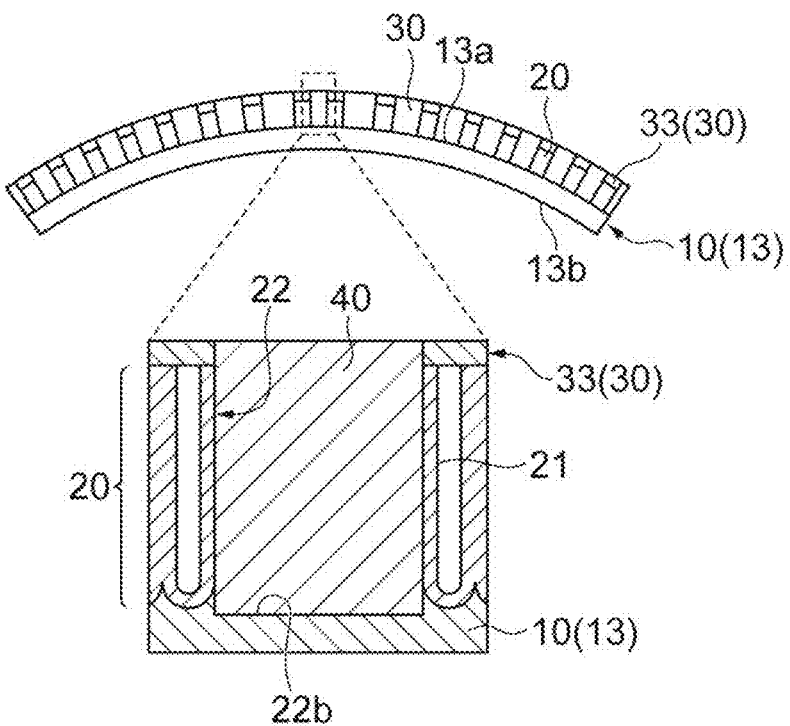

Next, a production method for the metal grid 1A of the embodiment will be described. FIGS. 7 and 8 are views illustrating a production step of the metal grid 1A. First, the planar metal plate 10 having a principal surface and a rear surface is prepared. Then, as illustrated in FIG. 7(a), the X-ray receiving portion 13 including the principal surface 13a and the rear surface 13b which are respectively curved is formed by bending the metal plate 10. The bending of the metal plate 10 is performed by, for example, pressing.

Figure 9:
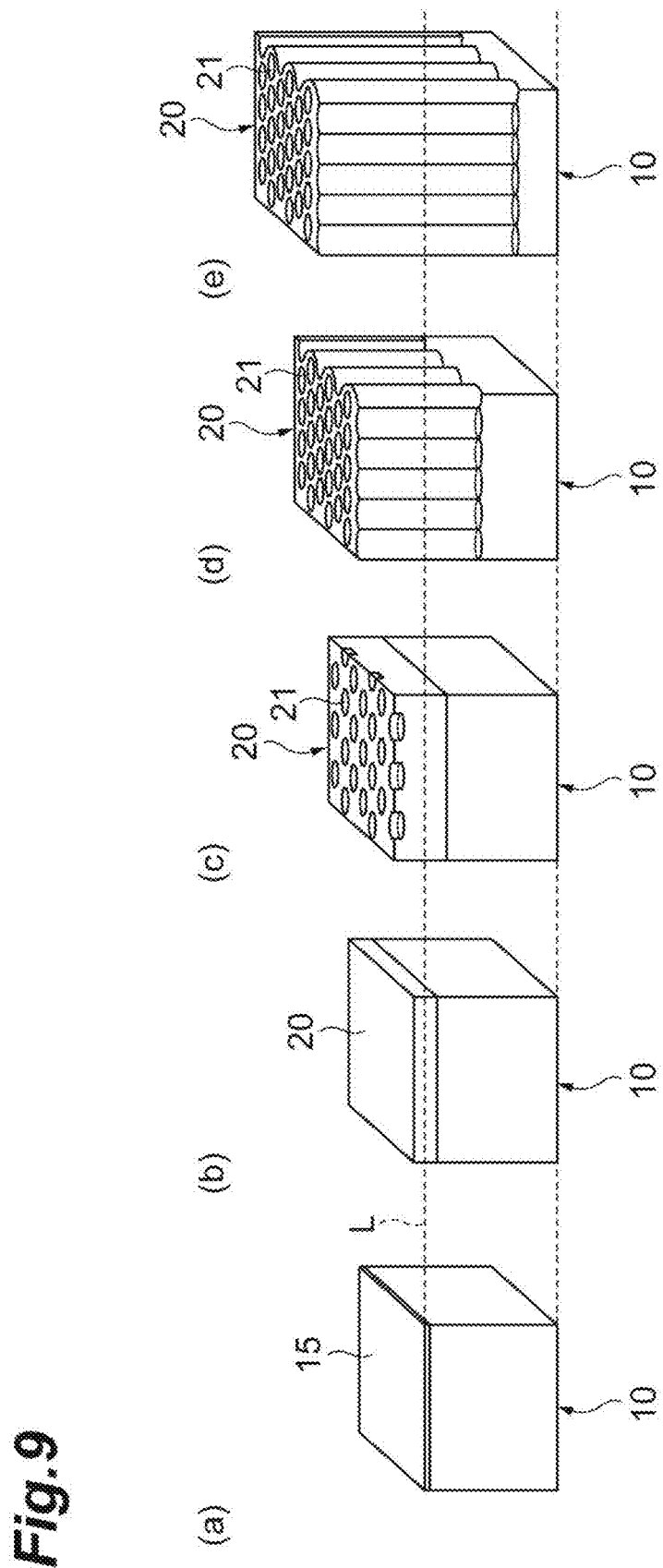
FIG. 9 is a view illustrating a progress of anodic oxidation.

Next, as illustrated in FIG. 7(b), an anodic oxidation treatment is performed on the principal surface 13a of the metal plate 10 so that the anodic oxide film 20 is formed. FIG. 9 is a view illustrating the progress of anodic oxidation. A dashed line L illustrated in FIG. 9 indicates the position of the principal surface 13a of the metal plate 10 to be subjected to anodic oxidation. As illustrated in FIG. 9(a), a natural oxide film 15 which is oxidized by oxygen in air is formed in advance on the principal surface 13a of the metal plate 10. When the anodic oxidation treatment starts, the initial oxide film 20 grows on the principal surface 13a of the metal plate 10 as illustrated in FIG. 9(b). When the anodic oxidation treatment is further continued, the plurality of holes 21 are generated as illustrated in FIG. 9(c) at a time point in which the thickness of the oxide film 20 reaches 10 nm to 20 nm. Then, the dissolution and formation of the oxide film 20 occur together and the upward growth and the downward growth of the plurality of holes 21 occur together (FIG. 9(d)). In this way, the anodic oxide film 20 including the plurality of holes 21 having a high aspect ratio and extending in a direction perpendicular to the principal surface 13a of the metal plate 10 is formed finally (FIG. 9(e)).

Next, as illustrated in FIG. 7(c), an etching mask 33 which is the protective film 30 having the periodic opening 31 is formed on the surface of the anodic oxide film 20. In this step, the etching mask 33 is formed by, for example, normal photolithography. Further, the opening width of the opening 31 of the etching mask 33 is set to be sufficiently larger than the inner diameter of each of the plurality of holes 21 of the anodic oxide film 20.

Next, as illustrated in FIG. 8(a), the anodic oxide film 20 is etched through the opening 31 of the etching mask 33.

Accordingly, a lattice structure with a periodic uneven shape is formed on the anodic oxide film 20. As an example, wet etching is performed on the anodic oxide film 20. For example, phosphoric acid is used as an etchant. As described above, since the anodic oxide film 20 includes the plurality of microscopic holes 21, the side surface of the concave portion 22 easily becomes perpendicular to the surface of the curved metal plate 10 when the etchant infiltrates into these holes 21 so that the side surface of the hole 21 is etched.

Next, the metal portion 40 is formed as illustrated in FIG. 8(b). In this step, the metal portion 40 is formed, for example, by vapor deposition such as physical vapor deposition or chemical vapor deposition or plating while the etching mask 33 is left. As an example, the metal portion 40 is formed by any one of electrolytic plating, chemical vapor deposition (CVD), and atomic layer deposition (ALD) in order to sufficiently infiltrate the metal into the concave portion 22 of the high aspect ratio. When the metal portion 40 is formed by electrolytic plating, the metal portion is electrically connected to the metal plate 10 exposed in the bottom surface 22b of the concave portion 22.

Finally, the frame portion 50 is attached to the flange portion 14 of the metal plate 10 to support the flange portion 14. In this way, the metal grid 1A of the embodiment is completed.

An effect obtained by the metal grid 1A of the embodiment and the production method thereof described above will be described. In the metal grid 1A of the embodiment, since the concave portion 22 is filled with the metal portion 40 of X-ray transmittance lower than that of the anodic oxide film 20, the inside of the concave portion 22 becomes an X-ray shielding region and the anodic oxide film 20 (the convex portion) remaining between the concave portions 22 becomes an X-ray passing region. Thus, it is possible to appropriately realize the metal X-ray grid 1A in which the X-ray passing region and the X-ray shielding region are periodically arranged.

Further, in the metal grid 1A of the embodiment, the principal surface 13a of the X-ray receiving portion 13 of the metal plate 10 is curved. Also in the production method of the embodiment, the principal surface 13a of the X-ray receiving portion 13 of the metal plate 10 is curved. Accordingly, the extension direction of the X-ray passing region is also slightly inclined in accordance with the curvature of the principal surface 13a. Thus, it is possible to decrease the relative angle between the traveling direction of the X-rays XL incident to the X-ray passing region and the extension direction of the X-ray passing region when receiving the X-rays XL radially spreading from the dot-shaped X-ray source (see FIG. 2) regardless of the distance from the center of the metal grid 1A by setting the curvature of the principal surface 13a in accordance with the distance from the X-ray source. Thus, according to the metal grid 1A and its production method of the embodiment, it is possible to obtain a desired function even at a position far from a center and to further widen an area of the metal grid where the X-rays XL are incident.

Further, as in the embodiment, the side surface 22a of the concave portion 22 may be perpendicular to the principal surface 13a of the X-ray receiving portion 13. Accordingly, the X-rays XL can efficiently pass in the X-ray passing region.

Further, as in the embodiment, the metal grid 1A may include the frame portion 50 which supports the flange portion 14 of the metal plate 10. Further, the production method for the metal grid 1A may include a step of attaching the frame portion 50 supporting the flange portion 14 of the metal plate 10. Accordingly, since the mechanical strength of the metal grid 1A can be maintained even when the metal plate 10 is thin, it is possible to reduce the loss of the X-rays XL when the X-rays are transmitted through the metal plate 10 while thinning the metal plate 10.

Further, as in the embodiment, the metal grid 1A may include the metal portion 40 which contains metal of X-ray transmittance lower than that of the valve metal of the metal plate 10 and fills the concave portion 22. Further, the production method for the metal grid 1A may further include a step of forming the metal portion 40 after the step of forming the concave portion 22. As described above, in this case, the metal portion 40 (the concave portion 22) becomes an X-ray shielding region and the anodic oxide film 20 between the metal portions 40 becomes an X-ray passing region. Then, also in such a case, the effect obtained by the above-described metal grid 1A can be appropriately achieved.

Further, as in the embodiment, the metal grid 1A may include a protective film 30 provided on a region (that is, the convex portion) excluding the concave portion 22 of the anodic oxide film 20. Further, in the step of forming the metal portion 40 in the production method for the metal grid 1A, the metal portion 40 may be formed while the etching mask 33 is left. By using such a protective film 30 (the etching mask 33), it is possible to effectively prevent a variation in X-ray transmittance due to the foreign matter infiltrating into the hole 21 of the porous anodic oxide film 20. Further, it is possible to effectively prevent metal from infiltrating into the hole 21 of the porous anodic oxide film 20 by the protective film 30 (the etching mask 33) when forming the metal portion 40. Thus, it is possible to suppress deterioration of X-ray transmittance in the region (the X-ray passing region) of the anodic oxide film 20 between the metal portions 40. In general, the X-ray transmittance of the etching mask 33 used when etching the anodic oxide film 20 is extremely high. Thus, the loss of the X-rays XL is slight even when the etching mask 33 remains in the completed metal X-ray grid 1A. On the other hand, it is possible to reduce production cost by omitting the step of removing the etching mask 33 in the production step of the metal X-ray grid 1A.

Further, as in the embodiment, the protective film 30 (the etching mask 33) may contain resin. In this way, since the protective film 30 (the etching mask 33) contains a material of extremely high X-ray transmittance, it is possible to extremely reduce the loss of the X-rays XL when the X-rays are transmitted through the protective film 30 (the etching mask 33).

Further, as in the embodiment, in the step of forming the metal portion 40, the metal portion 40 may be formed by any one of electrolytic plating, CVD, and ALD. Accordingly, the metal portion 40 can be appropriately formed by allowing a metal material to easily infiltrate into a deep portion inside the concave portion 22 having a fine and high aspect ratio.

First Modified Example

Figure 10:
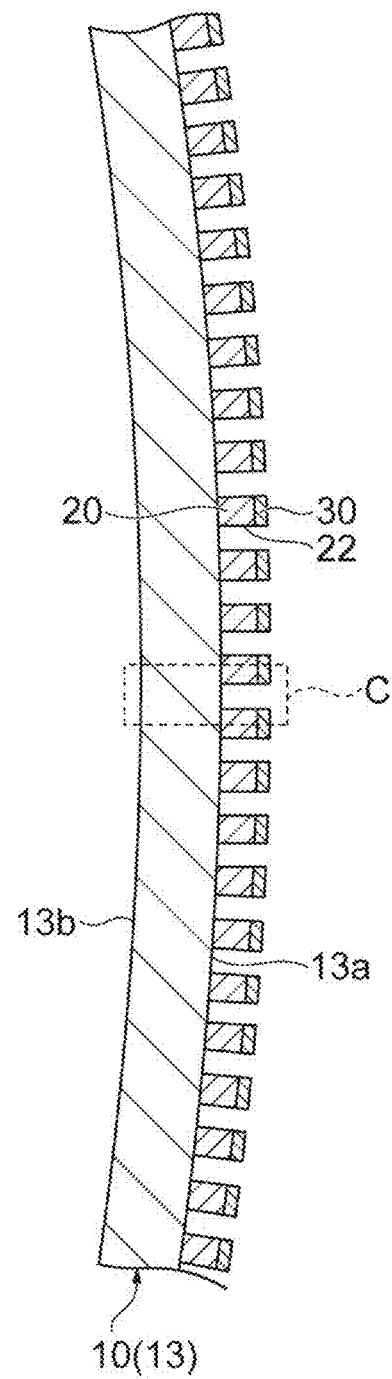
FIG. 10 is a cross-sectional view of a structure of an X-ray receiving portion of a metal plate according to a first modified example.
Figure 11:
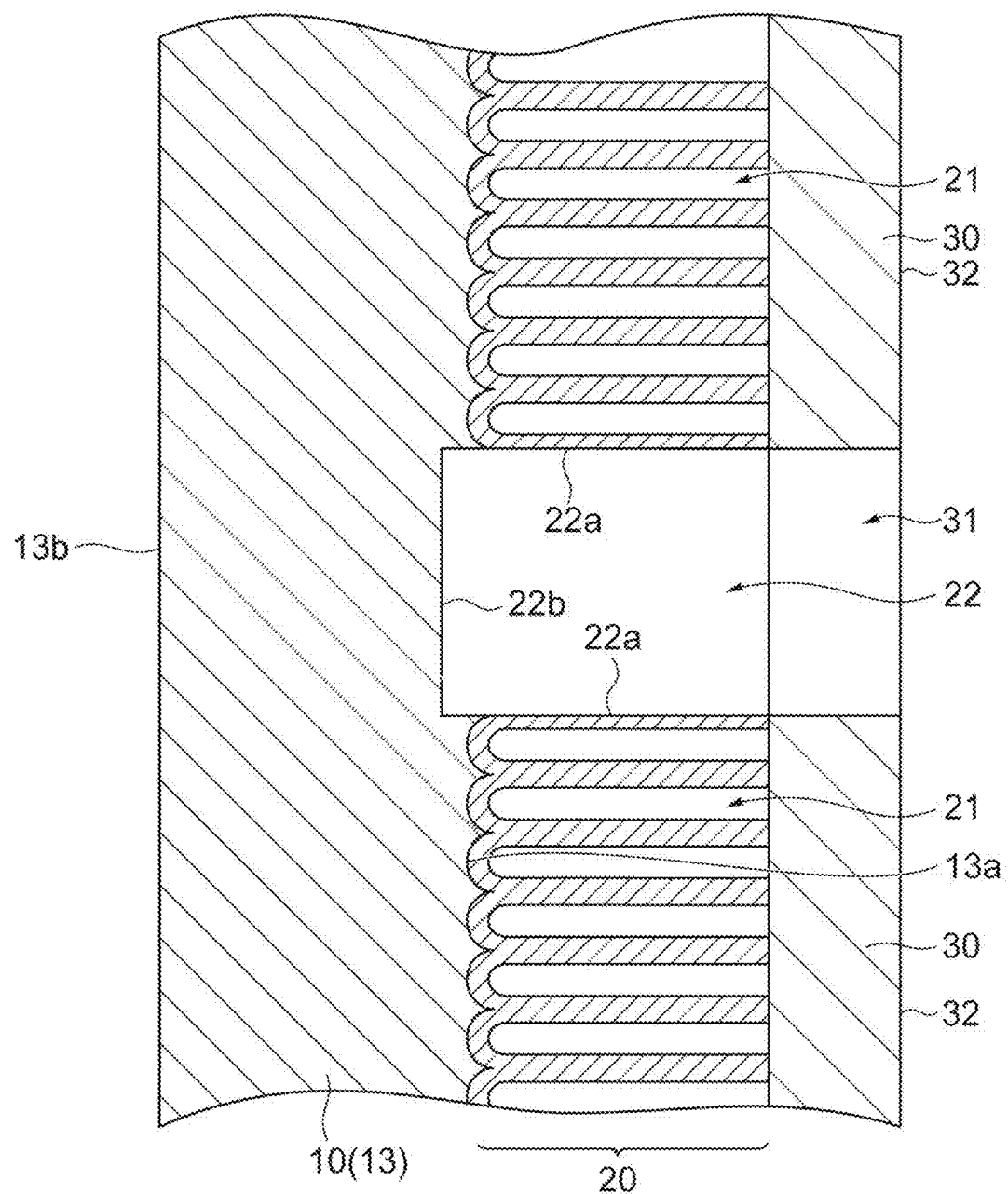
FIG. 11 is an enlarged cross-sectional view of a B part of FIG. 10.

Next, modified examples of the above-described embodiment will be described. FIG. 10 is a cross-sectional view illustrating a structure in the vicinity of the X-ray receiving portion 13 of the metal plate 10 according to a first modified example of the above-described embodiment. Further, FIG. 11 is an enlarged cross-sectional view of a C part of FIG. 10. As illustrated in these drawings, in the modified example, the metal portion 40 is not provided inside the concave portion 22 and the inside of the concave portion 22 is a void.

In this case, the concave portion 22 functions as the X-ray passing region and the anodic oxide film 20 and the protective film 30 between the concave portions 22 (alternately, surrounded by the concave portions 22) function as the X-ray shielding region.

As in the modified example, the metal grid 1A can exhibit a desired function even when the metal portion 40 is not provided. When producing such a metal grid 1A, the step of forming the metal portion 40 illustrated in FIG. 8(b) is omitted. Furthermore, even when the concave portion 22 is filled with a material of X-ray transmittance higher than that of the anodic oxide film 20 instead of the metal portion 40, the metal grid having the same function as that of the modified example can be obtained.

Second Modified Example

Figure 12:
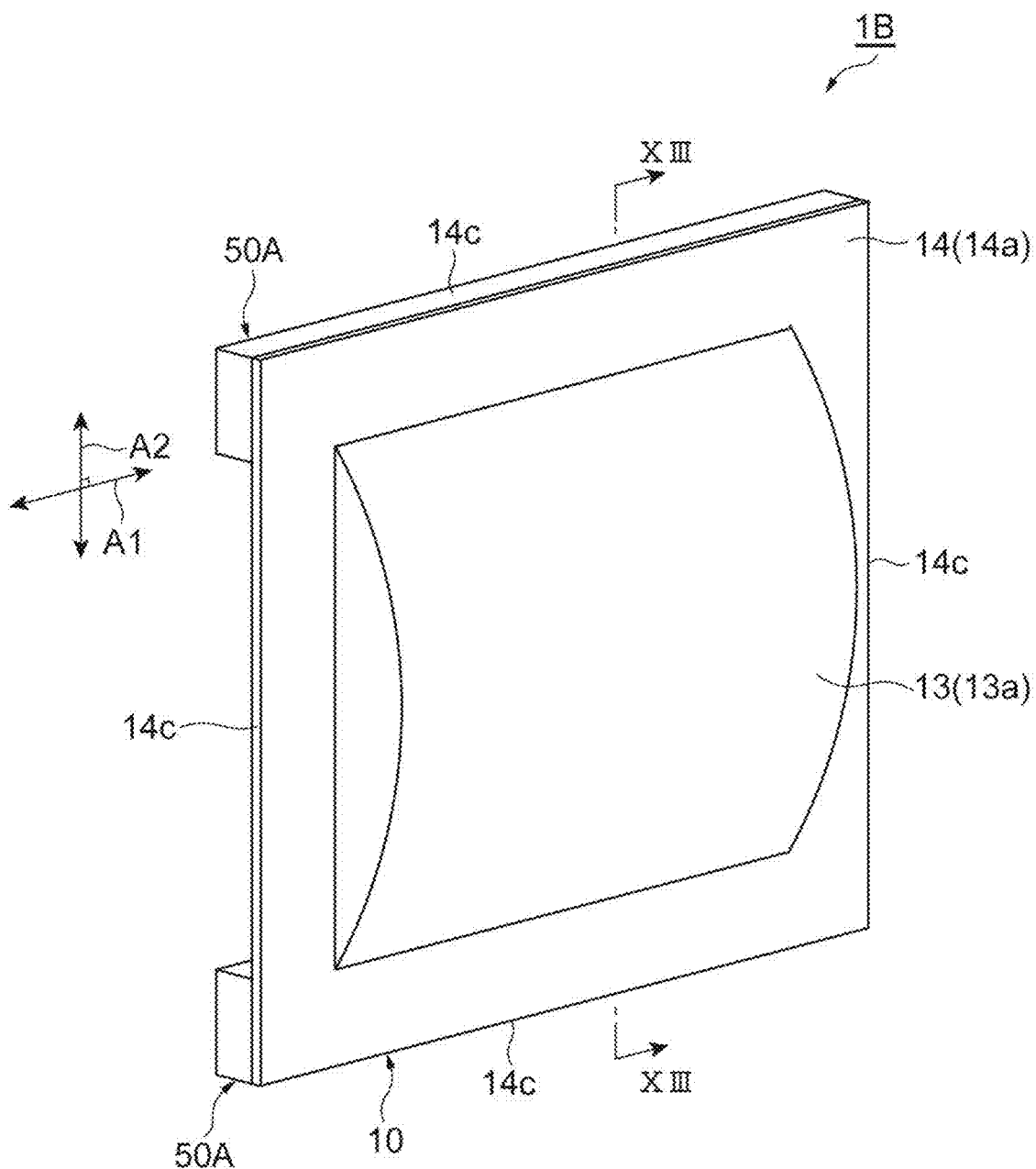
FIG. 12 is a perspective view illustrating an appearance of a metal grid according to a second modified example.
Figure 13:
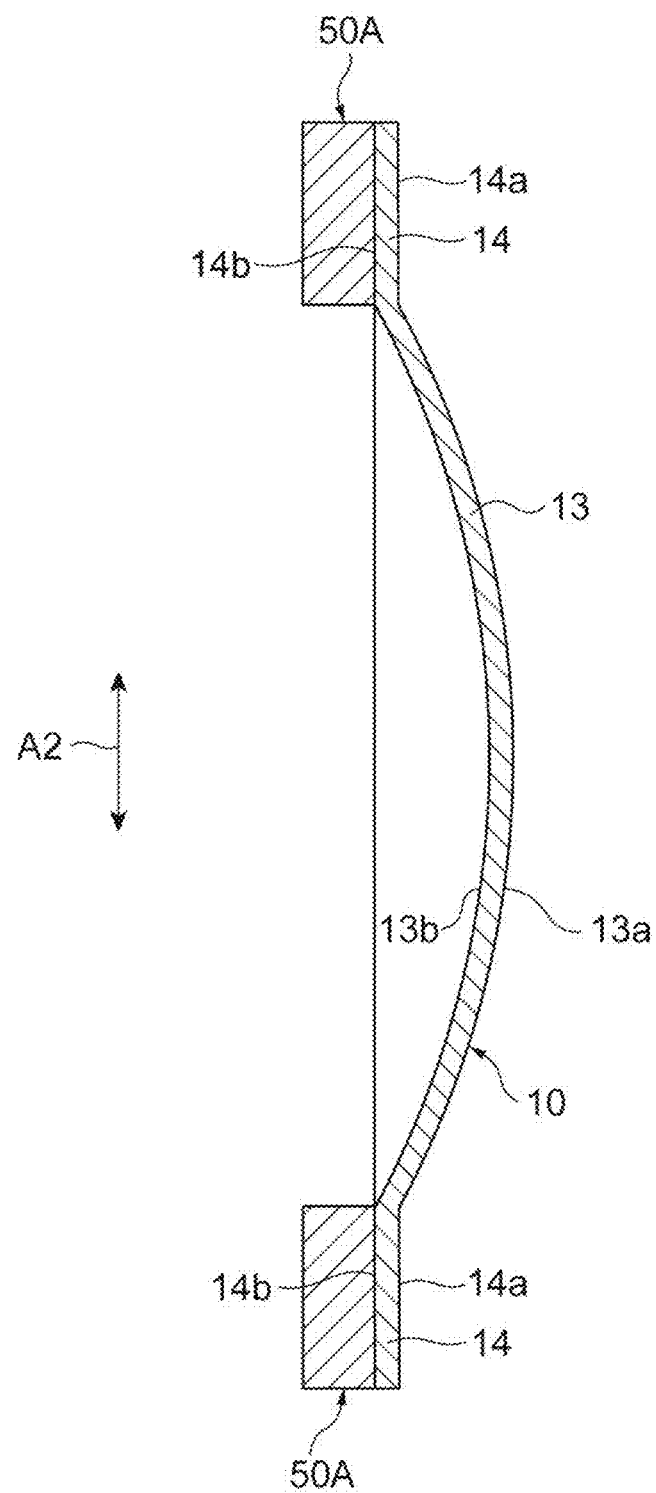
FIG. 13 is a cross-sectional view taken along a line XIII-XIII of FIG. 12.

FIG. 12 is a perspective view illustrating an appearance of a metal grid 1B according to a second modified example of the above-described embodiment. FIG. 13 is a cross-sectional view taken along a line XIII-XIII illustrated in FIG. 12. The modified example is different from the above-described embodiment in the shape of the frame portion. A frame portion 50A of the modified example is not a frame shape and is provided only in a part of the flange portion 14 of the metal plate 10. Specifically, the metal grid 1B of the modified example includes a pair of frame portions 50A which is symmetrically disposed with the X-ray receiving portion 13 interposed therebetween. The frame portions 50A extend in parallel to each other with the direction A1 along one side of the metal plate 10 (the direction along the cross-section where the X-ray receiving portion 13 is not curved) as a longitudinal direction and are arranged in the direction A2 intersecting the direction A1 (the direction along the cross-section where the X-ray receiving portion 13 is curved). When viewed from the normal direction of the metal plate 10 (a direction orthogonal to both of the directions A1 and A2), the X-ray receiving portion 13 is disposed between the pair of frame portions 50A. Furthermore, the configuration and the material other than those of the frame portion 50A described above are the same as those of the frame portion 50 of the above-described embodiment.

As in the modified example, the mechanical strength of the metal grid 1A can be maintained by supporting the flange portion 14 even when the frame portion 50A is provided only in a part of the flange portion 14. Furthermore, in the modified example, the pair of frame portions 50 extending along the direction A1 is arranged in the direction AZ but the pair of frame portions 50 extending along the direction A2 may be arranged in the direction A1.

Third Modified Example

Figure 14:
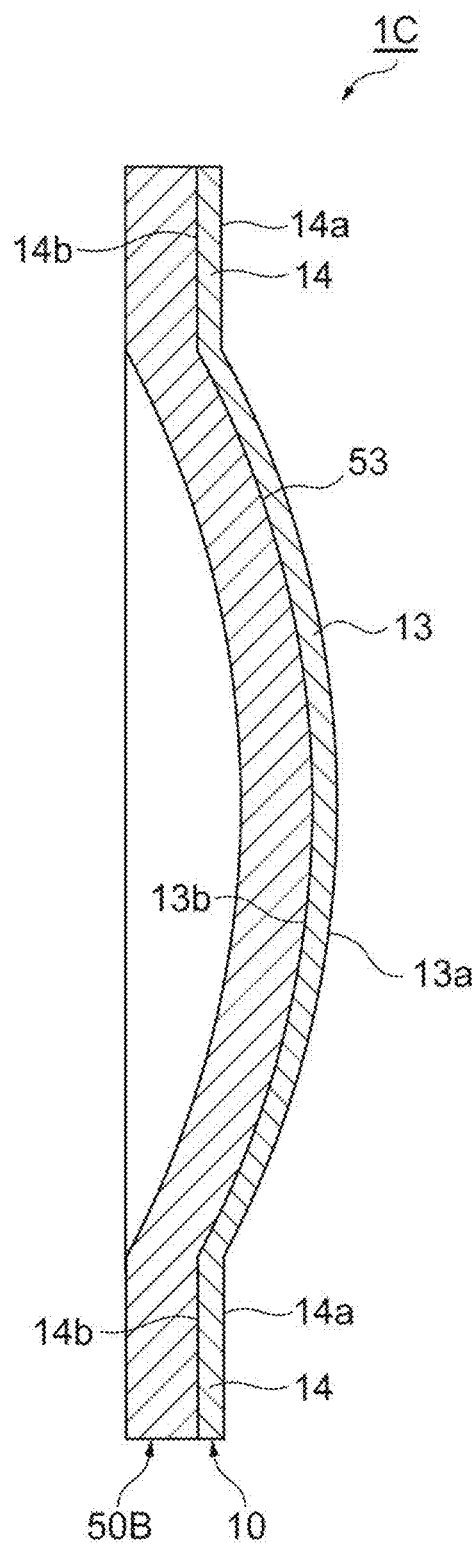
FIG. 14 is a cross-sectional view of a metal grid according to a third modified example.

FIG. 14 is a cross-sectional view of a metal grid 1C according to a third modified example of the above-described embodiment. The metal grid 1C of the modified example includes a support substrate 50B instead of the frame portion 50 of the above-described embodiment. The support substrate 50B includes a surface 53 having the same shape as that of the metal plate 10 and the metal plate 10 is affixed to the surface 53. Specifically, the support substrate 50B has the same planar shape as that of the metal plate 10 and is affixed to the X-ray receiving portion 13 and the flange portion 14 through an adhesive without any gap. Accordingly, the metal plate 10 is supported by the support substrate 50B and the mechanical strength of the metal grid 1C is maintained. As the material of the support substrate 50B, a material (a light element) of high X-ray transmittance is selected differently from the frame portion 50 of the above-described embodiment. This is because the support substrate SOB is also provided in the X-ray receiving portion 13 and the X-rays XL need to be efficiently transmitted through the support substrate 50B. As an example, CFRP is exemplified as the material of the support substrate SOB. The thickness of the support substrate 50B is, for example, 0.5 mm or more and 10 cm or less. Furthermore, the support substrate 50B of the modified example can appropriately support the metal plate 10 even when the metal plate 10 does not include the flange portion 14 differently from the frame portion 50 of the above-described embodiment. When producing the metal grid 1C of the modified example, the support substrate 50B may be attached to the metal plate 10 instead of the frame portion 50 in the step of attaching the frame portion 50 of the above-described embodiment. Further, in FIG. 14, the support substrate 50B is provided on the side of the rear surface 13b in the metal plate 10, but the support substrate 50B may be provided on the side of the principal surface 13a in the metal plate 10.

Fourth Modified Example

Figure 15:
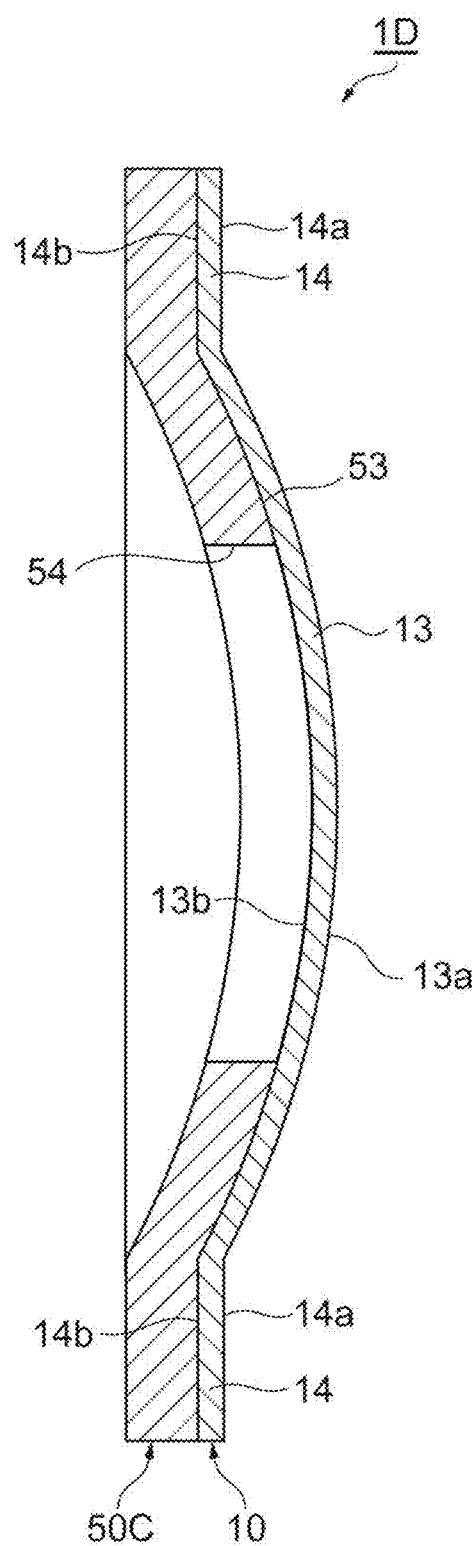
FIG. 15 is a cross-sectional view of a metal grid according to a fourth modified example.

FIG. 15 is a cross-sectional view of a metal grid 1D according to a fourth modified example of the above-described embodiment. The metal grid 1D of the modified example includes a support substrate 50C instead of the frame portion 50 of the above-described embodiment. The support substrate 50C includes a surface 53 having the same shape as that of the metal plate 10 and the metal plate 10 is affixed to the surface 53. Accordingly, the metal plate 10 is supported by the support substrate 50C and the mechanical strength of the metal grid 1D is maintained. However, the support substrate 50C of the modified example includes an opening 54 which is formed in a portion including the center of the X-ray receiving portion 13 differently from the third modified example. When viewed from the normal direction of the metal plate 10, the planar shape of the opening 54 is similar to the planar shape of the X-ray receiving portion 13 and is, for example, rectangular or square. According to the modified example, it is possible to avoid the attenuation of the X-rays XL due to the support substrate SOC by passing the X-rays XL in the opening 54 while supporting the metal plate 10 by the support substrate 50C. Furthermore, the support substrate 50C of the modified example can also appropriately support the metal plate 10 even when the metal plate 10 does not include the flange portion 14. When producing the metal grid 1D of the modified example, the support substrate 50C may be attached to the metal plate 10 instead of the frame portion 50 in the step of attaching the frame portion 50 of the above-described embodiment. Further, in FIG. 15, the support substrate 50C is provided on the side of the rear surface 13b in the metal plate 10, but the support substrate SOC may be provided on the side of the principal surface 13a in the metal plate 10.

Fifth Modified Example

Figure 16:
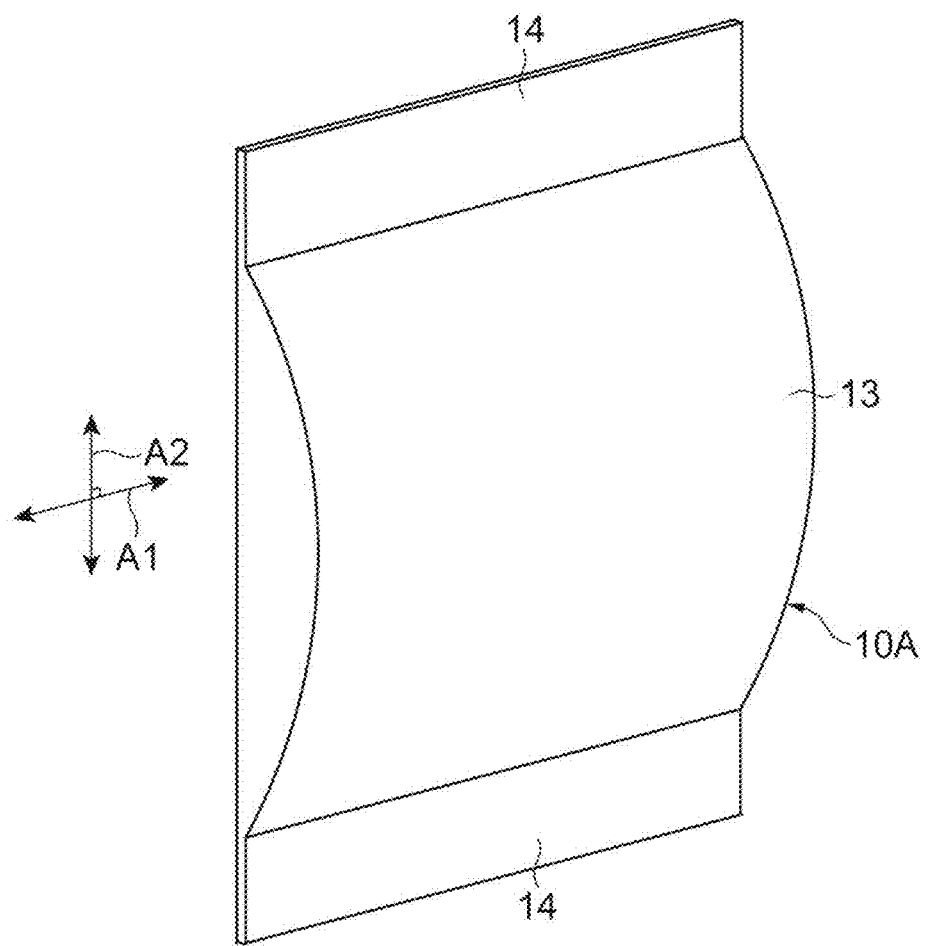
FIG. 16 is a perspective view of a metal plate according to a fifth modified example.

FIG. 16 is a perspective view illustrating a metal plate 10A according to a fifth modified example of the above-described embodiment. The metal plate 10A illustrated in the same drawing includes the flange portions 14 only at both ends in the direction A2 differently from the metal plate 10 of the above-described embodiment. Also in such a configuration, for example, when the pair of frame portions 50A (see FIGS. 12 and 13) shown in the second modified example is affixed to the flange portions 14, the mechanical strength of the metal grid can be appropriately maintained. Furthermore, the metal plate 10A may include the flange portions 14 only at both ends of the direction A1.

Sixth Modified Example

Figure 17:
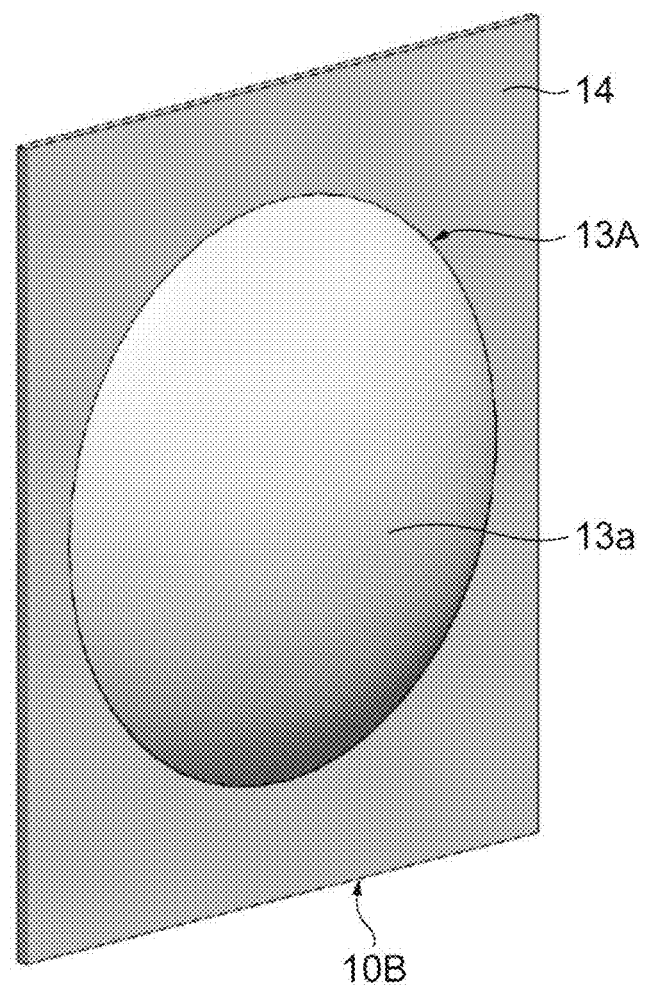
FIG. 17 is a perspective view of a metal plate according to a sixth modified example.
Figure 18:
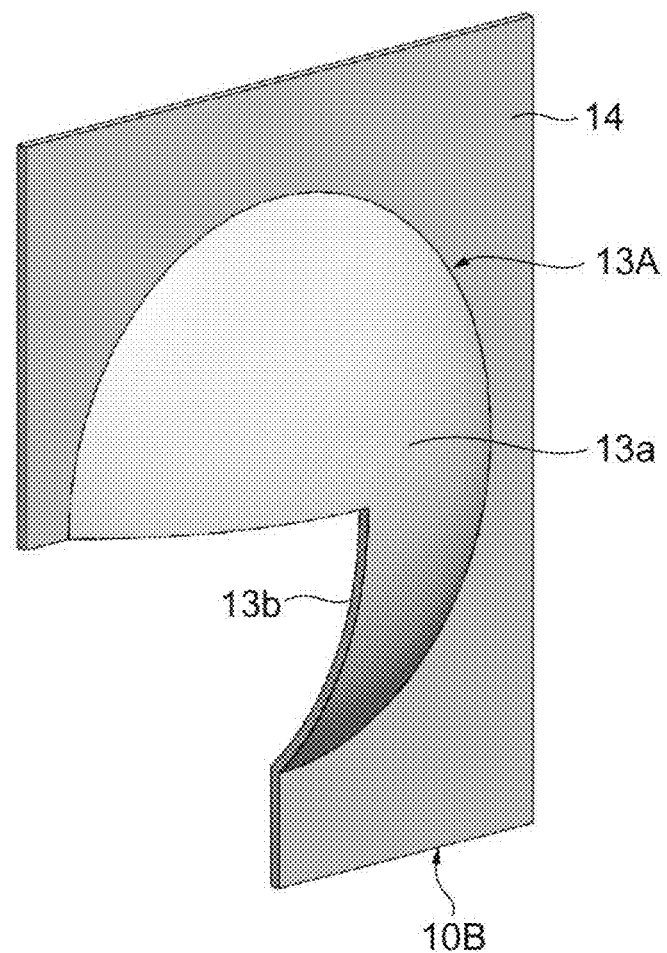
FIG. 18 is a perspective view illustrating the partially notched metal plate illustrated in FIG. 17.

FIG. 17 is a perspective view illustrating a metal plate 10B according to a sixth modified example of the above-described embodiment. FIG. 18 is a perspective view illustrating the partially notched metal plate 10B illustrated in FIG. 17. The metal plate 10B illustrated in these drawings is different from the metal plate 10 of the above-described embodiment in the shape of the X-ray receiving portion. The principal surface 13a and the rear surface 13b of the X-ray receiving portion 13A of the modified example have a two-dimensional curvature. That is, the principal surface 13a and the rear surface 13b of the X-ray receiving portion 13A in one cross-section including the optical axis of the X-ray XL have a curvature and the principal surface 13a and the rear surface 13b of the X-ray receiving portion 13A have a curvature also in a different cross-section including the optical axis of the X-ray XL and perpendicular to the one cross-section. As an example, the shapes of the principal surface 13a and the rear surface 13b of the X-ray receiving portion 13A are spherical. Further, the planar shape of the X-ray receiving portion 13 when viewed from the normal direction of the metal plate 10 is circular.

Seventh Modified Example

Figure 19:
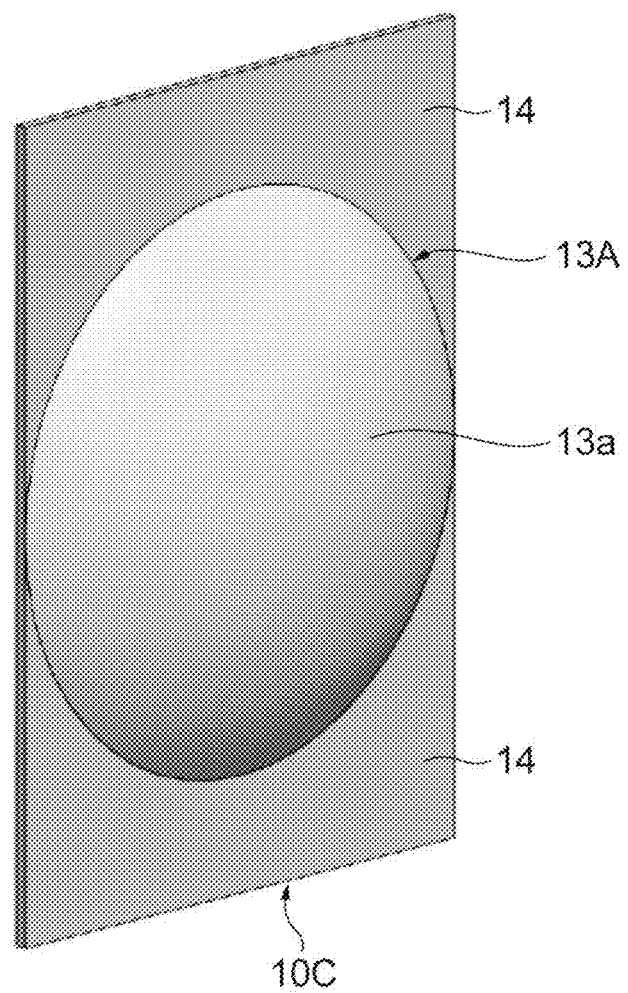
FIG. 19 is a perspective view of a metal plate according to a seventh modified example.

FIG. 19 is a perspective view of a metal plate 10C according to a seventh modified example of the above-described embodiment. The metal plate 10C illustrated in the same drawing includes the flange portions 14 only at both ends in a certain direction differently from the metal plate 10B of the sixth modified example. Also in such a configuration, for example, when a pair of frame portions 50A (see FIGS. 12 and 13) shown in the second modified example is affixed to the flange portions 14, the mechanical strength of the metal grid can be appropriately maintained.

Second Embodiment

Figure 20:
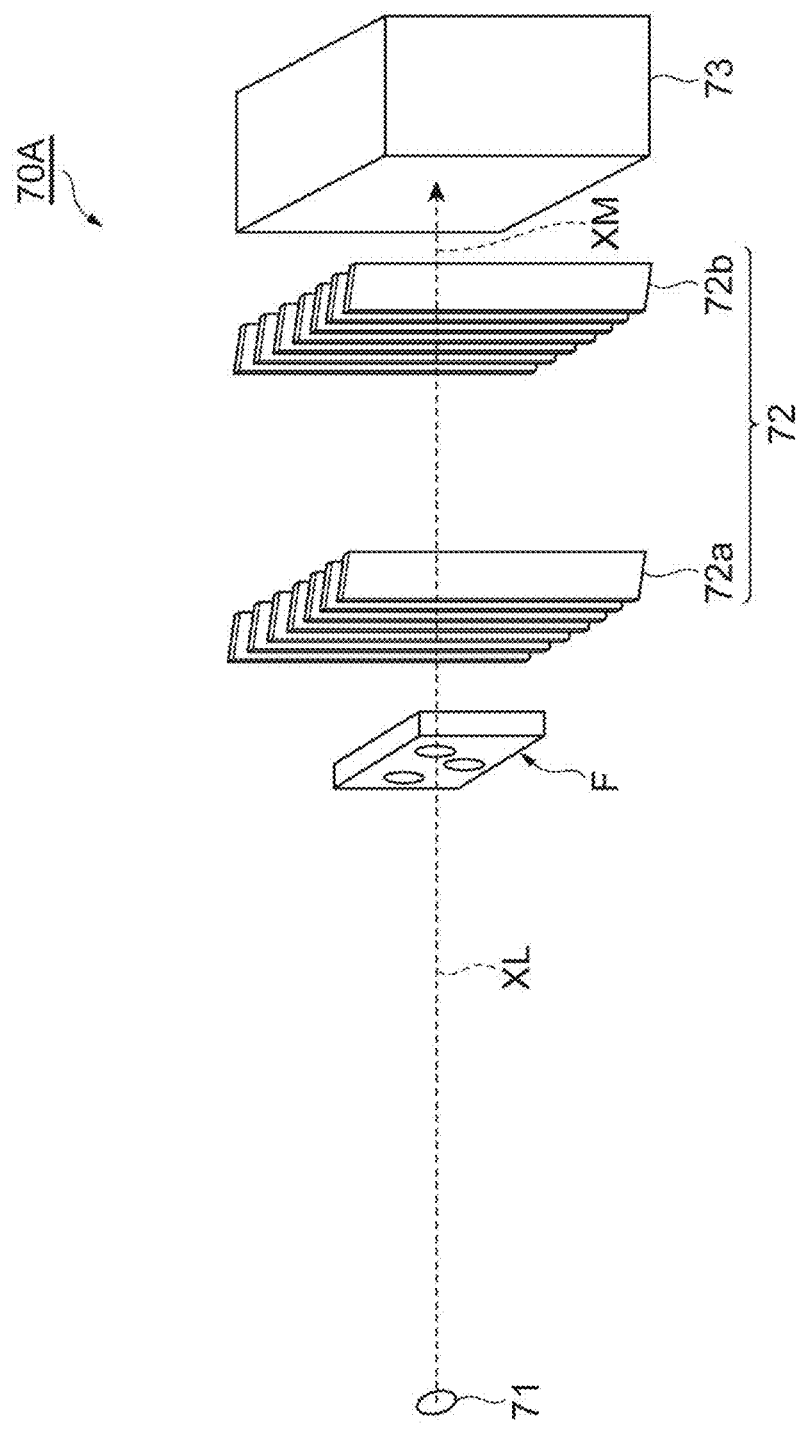
FIG. 20 is a view illustrating a configuration of an X-ray imaging device according to an embodiment of the invention.

FIG. 20 is a view illustrating a configuration of an X-ray imaging device 70A according to an embodiment of the invention. The X-ray imaging device 70A of the embodiment includes an X-ray source 71 which emits X-rays XL, a Talbot interferometer 72 which is irradiated with the X-rays XL emitted from the X-ray source 71, and an X-ray imaging unit 73 which captures an X-ray image XM emitted from the Talbot interferometer 72. The sample F which is a target to be captured is disposed between the X-ray source 71 and the Talbot interferometer 72. The Talbot interferometer 72 includes two metal grids 72a and 72b. These metal grids 72a and 72b are any one of the metal grids of the first embodiment and the first to seventh modified examples. According to the X-ray imaging device 70A of the modified example, since an area where the X-rays XL can be incident in the Talbot interferometer 72 is widened, a larger area can be captured.

Third Embodiment

Figure 21:
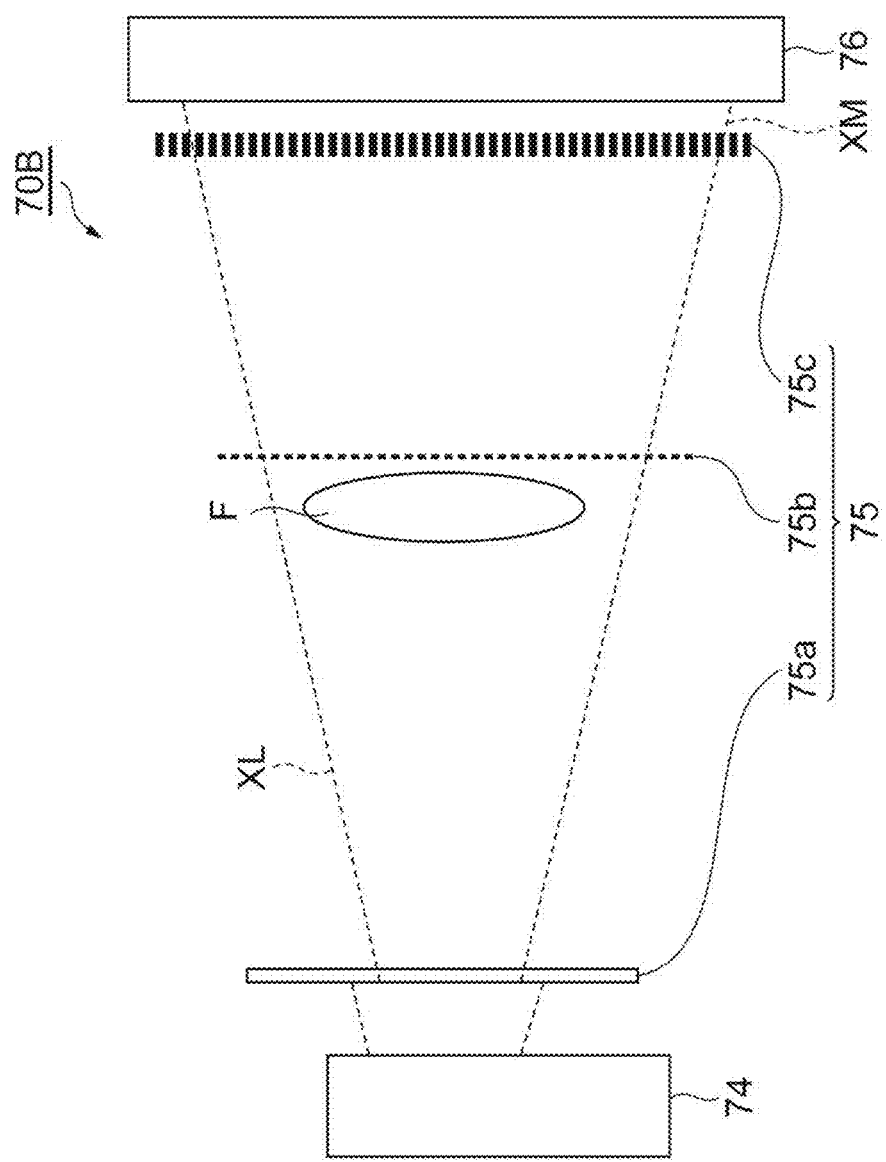
FIG. 21 is a view illustrating a configuration of an X-ray imaging device according to another embodiment of the invention.
Figure 22:
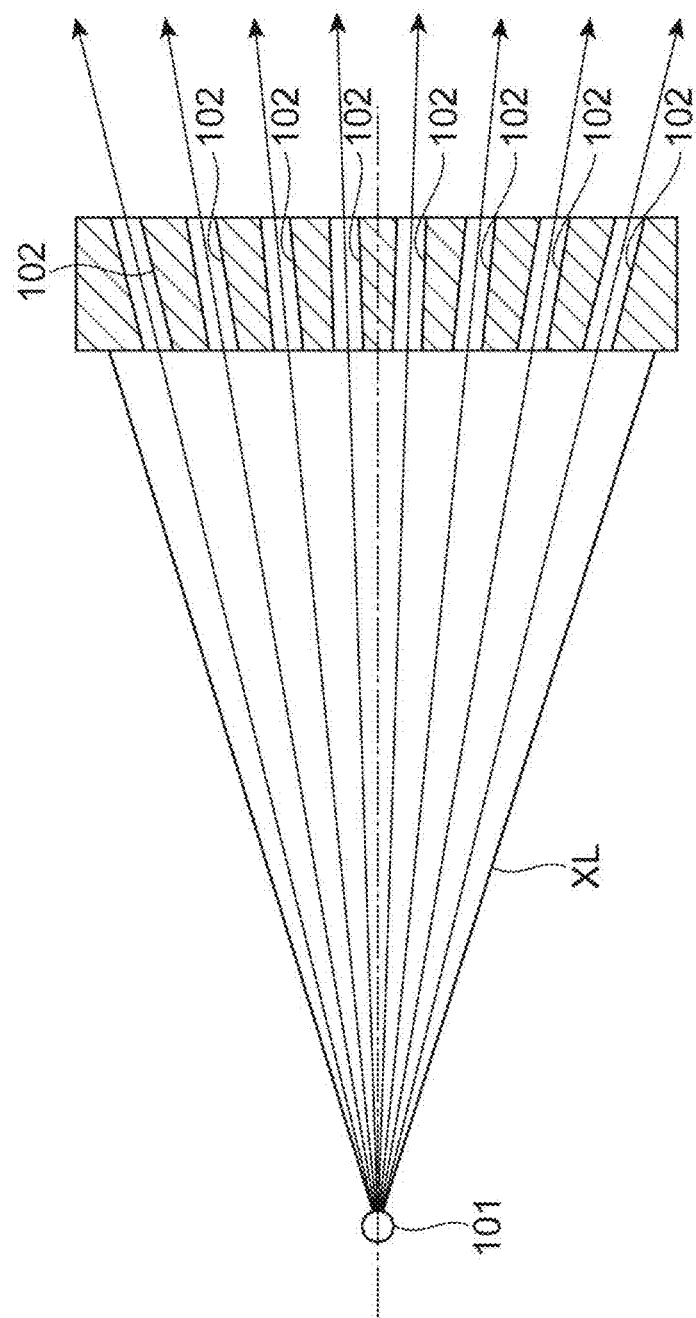
FIG. 22 is a view illustrating a configuration described in Patent Literature 1.

FIG. 21 is a view illustrating a configuration of an X-ray imaging device 70B according to another embodiment of the invention. The X-ray imaging device 70B of the embodiment includes an X-ray source 74 which emits X-rays XL, a Talbot-Lau interferometer 75 which is irradiated with the X-rays XL emitted from the X-ray source 74, and an X-ray imaging unit 76 which captures an X-ray image XM emitted from the Talbot-Lau interferometer 75. The Talbot-Lau interferometer 75 includes three metal grids (a first metal grid 75a, a second metal grid 75b, and a third metal grid 75c from the side close to the X-ray source 74). The sample F which is a target to be captured is disposed between the first metal grid 75a and the second metal grid 75b. Three metal grids 75a to 75c are any one of the metal grids of the first embodiment and the first to seventh modified examples. As an example, the metal grid (for example, the metal grid 1A of the first embodiment) with the metal portion 40 is used as the first metal grid 75a and the third metal grid 75c and the metal grid (for example, the metal grid of the first modified example) without the metal portion 40 is used as the second metal grid 75b. According to the X-ray imaging device 70B of the modified example, since an area where the X-rays XL can be incident in the Talbot-Lau interferometer 75 is widened, a larger area can be captured.

The metal X-ray grid, the X-ray imaging device, and the production method for the metal X-ray grid according to the invention are not limited to those of the embodiments and the modified examples described above and can be modified into various other forms. For example, the embodiments and the modified examples described above may be combined in accordance with the necessary objects and effects. Further, in the embodiments and the modified examples described above, one of the frame portion and the support substrate is attached to the metal plate, but both of the frame portion and the support substrate may be attached to the metal plate. Further, the frame portion and the support substrate may not be necessarily attached to a surface without the anodic oxide film and may be attached to a surface with the anodic oxide film through the anodic oxide film.

Further, in the embodiments and the modified examples described above, the surface at the outer side (the convex side) of the curved metal plate is defined as the principal surface, but the surface at the inner side (the concave side) of the curved metal plate may be defined as the principal surface. In that case, the anodic oxide film is formed on the surface at the inner side (the concave side) of the metal plate. Also in such a configuration, the effects of the embodiments and the modified examples described above can be appropriately achieved. However, there is an advantage that the etching mask is easily formed when the anodic oxide film is formed on the surface at the outer side (the convex side) of the curved metal plate.

REFERENCE SIGNS LIST 1A, 1B, 1C, 1D: metal grid, 10, 10A, 10B, 10C: metal plate, 13, 13A: X-ray receiving portion, 13a: principal surface, 13b: rear surface, 14: flange portion, 14a: principal surface, 14b: rear surface, 14c: outer edge, 15: natural oxide film, 20: anodic oxide film, 21: hole, 22: concave portion, 30: protective film, 31: opening, 33: etching mask, 40: metal portion, 50, 50A: frame portion, 50B, 50C: support substrate, 51: outer edge, 52: inner edge, 53: surface, 54: opening, 70A, 70B: X-ray imaging device, 71, 74: X-ray source, 72: Talbot interferometer, 72a, 72b: metal grid, 73, 76: X-ray imaging unit, 74: X-ray source, 75: Talbot-Lau interferometer, 75a, 75b, 75c: metal grid, F: sample, XL: X-ray, XM: X-ray image.

The invention claimed is:

1. A metal X-ray grid comprising:
    a valve metal plate which includes a curved principal surface;
    an anodic oxide film which is formed on the principal surface of the valve metal plate; and
    a lattice structure which has an uneven shape periodically formed on the anodic oxide film,
    wherein one or more concave portions constituting the uneven shape extend in a direction perpendicular to the principle surface, and
    wherein a side surface of the one or more concave portions is perpendicular to the principal surface.

2. The metal X-ray grid according to claim 1, further comprising:
    at least one of a frame portion which supports a peripheral edge portion of the valve metal plate and a support substrate which is affixed to the valve metal plate and supports the valve metal plate.

3. The metal X-ray grid according to claim 1, further comprising:
    a metal portion which contains metal of X-ray transmittance lower than that of valve metal of the valve metal plate and fills the concave portion of the lattice structure.

4. The metal X-ray grid according to claim 1, further comprising:
    a protective film which is provided on a region excluding a concave portion of the anodic oxide film.

5. The metal X-ray grid according to claim 4,
    wherein the protective film contains resin.

6. An X-ray imaging device comprising:
    an X-ray source which emits X-rays;
    a Talbot interferometer or a Talbot-Lau interferometer which is irradiated with the X-rays emitted from the X-ray source; and
    an X-ray imaging unit which captures an X-ray image emitted from the Talbot interferometer or the Talbot-Lau interferometer,
    wherein the Talbot interferometer or the Talbot-Lau interferometer includes the metal X-ray grid according to claim 1.

7. A production method for a metal X-ray grid comprising:
    a step of bending a valve metal plate including a principal surface such that the principal surface is curved;
    a step of forming an anodic oxide film on the principal surface of the valve metal plate; and
    a step of forming a lattice structure with a periodic uneven shape on the anodic oxide film by forming an etching mask with a periodic opening on a surface of the anodic oxide film and etching the anodic oxide film through the opening,
    wherein one or more concave portions constituting the uneven shape extend in a direction perpendicular to the principle surface, and
    wherein a side surface of the one or more concave portions is perpendicular to the principal surface.

8. The production method for the metal X-ray grid according to claim 7, further comprising:
    a step of forming a metal portion which contains metal of X-ray transmittance lower than that of valve metal of the valve metal plate and fills the concave portion of the lattice structure after the step of forming the lattice structure.

9. The production method for the metal X-ray grid according to claim 8,
    wherein in the step of forming the metal portion, the metal portion is formed while the etching mask is left.

10. The production method for the metal X-ray grid according to claim 8,
    wherein in the step of forming the metal portion, the metal portion is formed by any one of electrolytic plating, CVD, and ALD.

11. The production method for the metal X-ray grid according to claim 8, further comprising:
    a step of attaching at least one of a frame portion which supports a peripheral edge portion of the valve metal plate and a support substrate which is affixed to the valve metal plate and supports the valve metal plate.

* * * * *